United States Patent
Benary et al.

(10) Patent No.: US 8,574,287 B2
(45) Date of Patent: Nov. 5, 2013

(54) STENTS INCORPORATING A PLURALITY OF STRAIN-DISTRIBUTION LOCATIONS

(75) Inventors: Raphael Benary, Tel Aviv (IL); Alon Shalev, Ra'anana (IL)

(73) Assignee: Endospan Ltd., Herzilyia Pituach (IL)

( * ) Notice: Subject to any disclaimer, the term of this patent is extended or adjusted under 35 U.S.C. 154(b) by 0 days.

(21) Appl. No.: 13/523,296

(22) Filed: Jun. 14, 2012

(65) Prior Publication Data
US 2012/0323305 A1 Dec. 20, 2012

Related U.S. Application Data

(60) Provisional application No. 61/496,613, filed on Jun. 14, 2011.

(51) Int. Cl.
*A61F 2/06* (2013.01)
(52) U.S. Cl.
USPC ........................................ 623/1.15; 623/1.13
(58) Field of Classification Search
USPC ................................................ 623/1.13, 1.15
See application file for complete search history.

(56) References Cited

U.S. PATENT DOCUMENTS

| | | | |
|---|---|---|---|
| 4,355,426 A | 10/1982 | MacGregor |
| 4,505,767 A | 3/1985 | Quin |
| 4,562,596 A | 1/1986 | Kornberg |
| 4,577,631 A | 3/1986 | Kreamer |
| 4,617,932 A | 10/1986 | Kornberg |
| 4,665,906 A | 5/1987 | Jervis |
| 4,739,762 A | 4/1988 | Palmaz |
| 4,787,899 A | 11/1988 | Lazarus |
| 4,878,906 A | 11/1989 | Lindemann et al. |
| 4,886,062 A | 12/1989 | Wiktor |
| 4,938,740 A | 7/1990 | Melbin |
| 4,969,458 A | 11/1990 | Wiktor |
| 5,042,707 A | 8/1991 | Taheri |
| 5,064,435 A | 11/1991 | Porter |
| 5,104,404 A | 4/1992 | Wolff |

(Continued)

FOREIGN PATENT DOCUMENTS

| CA | 2 497 704 | 3/2004 |
|---|---|---|
| EP | 1177780 A2 | 2/2002 |

(Continued)

OTHER PUBLICATIONS

"E-vita® open plus" product brochure (JOTEC GmbH, Hechingen, Germany) (2010).

(Continued)

*Primary Examiner* — Thomas J Sweet
*Assistant Examiner* — Matthew Schall
(74) *Attorney, Agent, or Firm* — Sughrue Mion, PLLC

(57) ABSTRACT

A stent (120) has proximal and distal ends (140, 142), and is configured to assume radially-compressed and radially-expanded states. The stent (120) comprises a plurality of circumferential bands (122) disposed about a longitudinal axis (123) of the stent (120), each of which bands (122) comprises a plurality of struts (124) connected to one another. At least one of the bands (122) is shaped so as to define a plurality of distally-directed peaks (126) alternating with a plurality of proximally-directed troughs (128), and one or more strain-concentration modules (132). Each of the modules (132) has a central axis (156) parallel to the longitudinal axis (123) of the stent (120), and comprises: (a) an open loop section (150), which comprises one of the distally-directed peaks (126); (b) a primary neck section (152); and (c) a secondary section (154). Other embodiments are also described.

25 Claims, 9 Drawing Sheets

(56) References Cited

U.S. PATENT DOCUMENTS

| | | |
|---|---|---|
| 5,122,136 A | 6/1992 | Guglielmi et al. |
| 5,133,732 A | 7/1992 | Wiktor |
| 5,234,448 A | 8/1993 | Wholey et al. |
| 5,486,183 A | 1/1996 | Middleman et al. |
| 5,507,769 A | 4/1996 | Marin et al. |
| 5,509,923 A | 4/1996 | Middleman et al. |
| 5,522,880 A | 6/1996 | Barone et al. |
| 5,527,322 A | 6/1996 | Klein et al. |
| 5,549,662 A | 8/1996 | Fordenbacher |
| 5,554,181 A | 9/1996 | Das |
| 5,556,413 A | 9/1996 | Lam |
| 5,562,724 A | 10/1996 | Vorwerk et al. |
| 5,607,445 A | 3/1997 | Summers |
| 5,613,974 A | 3/1997 | Andreas et al. |
| 5,632,746 A | 5/1997 | Middleman et al. |
| 5,632,763 A | 5/1997 | Glastra |
| 5,632,772 A | 5/1997 | Alcime et al. |
| 5,639,278 A | 6/1997 | Dereume et al. |
| 5,643,340 A | 7/1997 | Nunokawa |
| 5,653,743 A | 8/1997 | Martin |
| 5,676,696 A | 10/1997 | Marcade |
| 5,676,697 A | 10/1997 | McDonald |
| 5,728,134 A | 3/1998 | Barak |
| 5,749,879 A | 5/1998 | Middleman et al. |
| 5,755,770 A | 5/1998 | Ravenscroft |
| 5,755,771 A | 5/1998 | Penn et al. |
| 5,755,777 A | 5/1998 | Chuter |
| 5,755,781 A | 5/1998 | Jayaraman |
| 5,769,882 A | 6/1998 | Fogarty et al. |
| 5,769,884 A | 6/1998 | Solovay |
| 5,782,903 A | 7/1998 | Wiktor |
| 5,782,906 A | 7/1998 | Marshall et al. |
| 5,824,040 A | 10/1998 | Cox et al. |
| 5,827,321 A | 10/1998 | Roubin et al. |
| 5,843,170 A | 12/1998 | Ahn |
| 5,855,600 A | 1/1999 | Alt |
| 5,860,991 A | 1/1999 | Klein et al. |
| 5,876,432 A | 3/1999 | Lau et al. |
| 5,906,641 A | 5/1999 | Thompson et al. |
| 5,921,994 A | 7/1999 | Andreas et al. |
| 5,980,552 A | 11/1999 | Pinchasik et al. |
| 6,015,431 A | 1/2000 | Thornton et al. |
| 6,016,810 A | 1/2000 | Ravenscroft |
| 6,030,414 A | 2/2000 | Taheri |
| 6,033,435 A | 3/2000 | Penn et al. |
| 6,036,725 A | 3/2000 | Avellanet |
| 6,059,824 A | 5/2000 | Taheri |
| 6,099,497 A | 8/2000 | Adams et al. |
| 6,117,145 A | 9/2000 | Wood et al. |
| 6,156,064 A | 12/2000 | Chouinard |
| 6,200,339 B1 | 3/2001 | Leschinsky et al. |
| 6,206,893 B1 | 3/2001 | Klein et al. |
| 6,270,524 B1 | 8/2001 | Kim |
| 6,283,991 B1 | 9/2001 | Cox et al. |
| 6,290,720 B1 | 9/2001 | Khosravi et al. |
| 6,312,458 B1 | 11/2001 | Golds |
| 6,325,823 B1 | 12/2001 | Horzewski et al. |
| 6,344,056 B1 | 2/2002 | Dehdashtian |
| 6,428,565 B1 | 8/2002 | Wisselink |
| 6,506,211 B1 | 1/2003 | Skubitz et al. |
| 6,520,988 B1 | 2/2003 | Colombo et al. |
| 6,613,078 B1 | 9/2003 | Barone |
| 6,635,083 B1 | 10/2003 | Cheng et al. |
| 6,652,567 B1 | 11/2003 | Deaton |
| 6,656,214 B1 | 12/2003 | Fogarty et al. |
| 6,692,520 B1 | 2/2004 | Gambale et al. |
| 6,695,833 B1 | 2/2004 | Frantzen |
| 6,743,195 B2 | 6/2004 | Zucker |
| 6,752,826 B2 | 6/2004 | Holloway et al. |
| 6,776,794 B1 | 8/2004 | Hong et al. |
| 6,808,534 B1 | 10/2004 | Escano |
| 6,814,749 B2 | 11/2004 | Cox et al. |
| 6,814,752 B1 | 11/2004 | Chuter |
| 6,824,560 B2 | 11/2004 | Pelton |
| 6,846,321 B2 | 1/2005 | Zucker |
| 6,907,285 B2 | 6/2005 | Denker et al. |
| 6,908,477 B2 | 6/2005 | McGuckin, Jr. et al. |
| 6,929,660 B1 | 8/2005 | Ainsworth et al. |
| 6,942,691 B1 | 9/2005 | Chuter |
| 6,964,679 B1 | 11/2005 | Marcade et al. |
| 6,986,774 B2 | 1/2006 | Middleman et al. |
| 7,008,441 B2 | 3/2006 | Zucker |
| 7,044,962 B2 | 5/2006 | Elliott |
| 7,105,020 B2 | 9/2006 | Greenberg et al. |
| 7,112,217 B1 | 9/2006 | Kugler et al. |
| 7,115,127 B2 | 10/2006 | Lindenbaum et al. |
| 7,144,421 B2 | 12/2006 | Carpenter et al. |
| 7,198,638 B2 | 4/2007 | Dong |
| 7,201,772 B2 | 4/2007 | Schwammenthal |
| 7,223,266 B2 | 5/2007 | Lindenbaum et al. |
| 7,279,003 B2 | 10/2007 | Berra et al. |
| 7,294,145 B2 | 11/2007 | Ward |
| 7,306,623 B2 | 12/2007 | Watson |
| 7,341,598 B2 | 3/2008 | Davidson et al. |
| 7,407,509 B2 | 8/2008 | Greenberg et al. |
| 7,429,269 B2 | 9/2008 | Schwammenthal |
| 7,442,204 B2 | 10/2008 | Schwammenthal |
| 7,473,272 B2 | 1/2009 | Pryor |
| 7,537,609 B2 | 5/2009 | Davidson et al. |
| 7,540,881 B2 | 6/2009 | Meyer et al. |
| 7,544,160 B2 | 6/2009 | Gross |
| 7,637,939 B2 | 12/2009 | Tischler |
| 7,662,161 B2 | 2/2010 | Briganti et al. |
| 7,662,168 B2 | 2/2010 | McGuckin, Jr. et al. |
| 7,678,141 B2 | 3/2010 | Greenan et al. |
| 7,722,626 B2 | 5/2010 | Middleman et al. |
| 7,731,732 B2 | 6/2010 | Ken |
| 7,803,178 B2 | 9/2010 | Whirley et al. |
| 7,815,673 B2 | 10/2010 | Bloom et al. |
| 7,887,575 B2 | 2/2011 | Kujawski |
| 7,959,662 B2 | 6/2011 | Erbel et al. |
| 8,066,755 B2 | 11/2011 | Zacharias et al. |
| 8,080,053 B2 | 12/2011 | Satasiya et al. |
| 8,172,892 B2 | 5/2012 | Chuter et al. |
| 2001/0004705 A1 | 6/2001 | Killion et al. |
| 2001/0014823 A1 | 8/2001 | Ressemann et al. |
| 2001/0034550 A1 | 10/2001 | Buirge et al. |
| 2001/0044651 A1 | 11/2001 | Steinke et al. |
| 2001/0044652 A1 | 11/2001 | Moore |
| 2001/0047198 A1 | 11/2001 | Drasler et al. |
| 2001/0053930 A1 | 12/2001 | Kugler et al. |
| 2002/0040236 A1 | 4/2002 | Lau et al. |
| 2002/0099438 A1 | 7/2002 | Furst |
| 2002/0099441 A1 | 7/2002 | Dehdashtian |
| 2002/0107564 A1 | 8/2002 | Cox et al. |
| 2002/0123791 A1 | 9/2002 | Harrison |
| 2002/0156495 A1 | 10/2002 | Brenneman et al. |
| 2003/0040791 A1 | 2/2003 | Oktay |
| 2003/0074055 A1 | 4/2003 | Haverkost |
| 2003/0093145 A1 | 5/2003 | Lawrence-Brown et al. |
| 2003/0130720 A1 | 7/2003 | DePalma et al. |
| 2003/0144725 A1 | 7/2003 | Lombardi |
| 2003/0153968 A1 | 8/2003 | Geis et al. |
| 2003/0191523 A1 | 10/2003 | Hojeibane |
| 2003/0199967 A1 | 10/2003 | Hartley et al. |
| 2003/0199968 A1 | 10/2003 | Ainsworth et al. |
| 2003/0212449 A1 | 11/2003 | Cox |
| 2003/0236567 A1 | 12/2003 | Elliot |
| 2004/0015227 A1 | 1/2004 | Vardi et al. |
| 2004/0015229 A1 | 1/2004 | Fulkerson et al. |
| 2004/0098091 A1 | 5/2004 | Erbel et al. |
| 2004/0106972 A1 | 6/2004 | Deaton |
| 2004/0106978 A1 | 6/2004 | Greenberg et al. |
| 2004/0133266 A1 | 7/2004 | Clerc et al. |
| 2004/0171978 A1 | 9/2004 | Shalaby |
| 2004/0181149 A1 | 9/2004 | Langlotz et al. |
| 2004/0215327 A1 | 10/2004 | Doig et al. |
| 2005/0033406 A1 | 2/2005 | Barnhart et al. |
| 2005/0049678 A1 | 3/2005 | Cocks et al. |
| 2005/0065545 A1 | 3/2005 | Wallace |
| 2005/0085900 A1 | 4/2005 | Case et al. |
| 2005/0102018 A1 | 5/2005 | Carpenter et al. |
| 2005/0102021 A1 | 5/2005 | Osborne |
| 2005/0131517 A1 | 6/2005 | Hartley et al. |

(56) References Cited

U.S. PATENT DOCUMENTS

| | | |
|---|---|---|
| 2005/0149166 A1 | 7/2005 | Schaeffer et al. |
| 2005/0154448 A1 | 7/2005 | Cully et al. |
| 2005/0171598 A1 | 8/2005 | Schaeffer |
| 2005/0203606 A1 | 9/2005 | VanCamp |
| 2005/0222667 A1 | 10/2005 | Hunt |
| 2005/0222668 A1 | 10/2005 | Schaeffer et al. |
| 2005/0222669 A1 | 10/2005 | Purdy |
| 2005/0266042 A1 | 12/2005 | Tseng |
| 2005/0283188 A1 | 12/2005 | Loshakove et al. |
| 2006/0015170 A1 | 1/2006 | Jones et al. |
| 2006/0052799 A1 | 3/2006 | Middleman et al. |
| 2006/0069426 A1 | 3/2006 | Weinberger |
| 2006/0100684 A1 | 5/2006 | Elliott |
| 2006/0106406 A1 | 5/2006 | Weinberger |
| 2006/0149360 A1 | 7/2006 | Schwammenthal |
| 2006/0155358 A1 | 7/2006 | LaDuca et al. |
| 2006/0155366 A1 | 7/2006 | LaDuca et al. |
| 2006/0167476 A1 | 7/2006 | Burdulis, Jr. et al. |
| 2006/0173530 A1 | 8/2006 | Das |
| 2006/0193892 A1 | 8/2006 | Furst et al. |
| 2006/0229709 A1 | 10/2006 | Morris et al. |
| 2006/0241740 A1 | 10/2006 | Vardi et al. |
| 2006/0281966 A1 | 12/2006 | Peacock, III |
| 2007/0021822 A1 | 1/2007 | Boatman |
| 2007/0043425 A1 | 2/2007 | Hartley et al. |
| 2007/0050011 A1 | 3/2007 | Klein et al. |
| 2007/0055350 A1 | 3/2007 | Erickson et al. |
| 2007/0055358 A1 | 3/2007 | Krolik et al. |
| 2007/0060989 A1 | 3/2007 | Deem et al. |
| 2007/0061002 A1 | 3/2007 | Paul, Jr. et al. |
| 2007/0073373 A1 | 3/2007 | Bonsignore |
| 2007/0088425 A1 | 4/2007 | Schaeffer |
| 2007/0112344 A1 | 5/2007 | Keilman |
| 2007/0135677 A1 | 6/2007 | Miller et al. |
| 2007/0142896 A1 | 6/2007 | Anderson et al. |
| 2007/0150051 A1 | 6/2007 | Menardiere et al. |
| 2007/0156167 A1 | 7/2007 | Connors et al. |
| 2007/0167898 A1 | 7/2007 | Peters et al. |
| 2007/0167955 A1 | 7/2007 | Menardiere et al. |
| 2007/0168018 A1 | 7/2007 | Amplatz et al. |
| 2007/0179598 A1 | 8/2007 | Duerig |
| 2007/0185565 A1 | 8/2007 | Schwammenthal et al. |
| 2007/0208410 A1 | 9/2007 | Berra et al. |
| 2007/0213805 A1 | 9/2007 | Schaeffer et al. |
| 2007/0213807 A1 | 9/2007 | Roubin et al. |
| 2007/0219610 A1 | 9/2007 | Israel |
| 2007/0219627 A1 | 9/2007 | Chu |
| 2007/0233229 A1 | 10/2007 | Berra et al. |
| 2007/0237973 A1 | 10/2007 | Purdy et al. |
| 2007/0244542 A1 | 10/2007 | Greenan et al. |
| 2007/0244543 A1 | 10/2007 | Mitchell |
| 2007/0244547 A1 | 10/2007 | Greenan |
| 2007/0250154 A1 | 10/2007 | Greenberg et al. |
| 2007/0255388 A1 | 11/2007 | Rudakov et al. |
| 2008/0002871 A1 | 1/2008 | Gunzert-Marx et al. |
| 2008/0015673 A1 | 1/2008 | Chuter |
| 2008/0058918 A1 | 3/2008 | Watson |
| 2008/0109066 A1 | 5/2008 | Quinn |
| 2008/0114445 A1 | 5/2008 | Melsheimer et al. |
| 2008/0147173 A1 | 6/2008 | McIff et al. |
| 2008/0167704 A1 | 7/2008 | Wright et al. |
| 2008/0195190 A1 | 8/2008 | Bland et al. |
| 2008/0195191 A1 | 8/2008 | Luo et al. |
| 2008/0215134 A1 | 9/2008 | Lawrence/Brown |
| 2008/0249598 A1 | 10/2008 | Sherry |
| 2008/0269789 A1 | 10/2008 | Eli |
| 2008/0275540 A1 | 11/2008 | Wen |
| 2008/0275542 A1 | 11/2008 | LaDuca et al. |
| 2008/0288044 A1 | 11/2008 | Osborne |
| 2008/0300665 A1 | 12/2008 | Lootz et al. |
| 2008/0319528 A1 | 12/2008 | Yribarren et al. |
| 2009/0012597 A1 | 1/2009 | Doig et al. |
| 2009/0012602 A1 | 1/2009 | Quadri |
| 2009/0030502 A1 | 1/2009 | Sun et al. |
| 2009/0048663 A1 | 2/2009 | Greenberg |
| 2009/0054967 A1 | 2/2009 | Das |
| 2009/0062899 A1 | 3/2009 | Dang et al. |
| 2009/0069882 A1 | 3/2009 | Venturelli et al. |
| 2009/0082841 A1 | 3/2009 | Zacharias et al. |
| 2009/0099648 A1 | 4/2009 | Yu |
| 2009/0099649 A1 | 4/2009 | Chobotov et al. |
| 2009/0105809 A1 | 4/2009 | Lee et al. |
| 2009/0112233 A1 | 4/2009 | Xiao |
| 2009/0125096 A1 | 5/2009 | Chu et al. |
| 2009/0138067 A1 | 5/2009 | Pinchuk et al. |
| 2009/0149877 A1 | 6/2009 | Hanson et al. |
| 2009/0227997 A1 | 9/2009 | Wang et al. |
| 2009/0240316 A1 | 9/2009 | Bruszewski |
| 2009/0248134 A1 | 10/2009 | Dierking et al. |
| 2009/0254170 A1 | 10/2009 | Hartley et al. |
| 2009/0259290 A1 | 10/2009 | Bruszewski et al. |
| 2009/0287145 A1 | 11/2009 | Cragg et al. |
| 2010/0004728 A1 | 1/2010 | Rao et al. |
| 2010/0029608 A1 | 2/2010 | Finley et al. |
| 2010/0063575 A1 | 3/2010 | Shalev |
| 2010/0070019 A1 | 3/2010 | Shalev |
| 2010/0082091 A1 | 4/2010 | Berez et al. |
| 2010/0161026 A1 | 6/2010 | Brocker et al. |
| 2010/0211159 A1 | 8/2010 | Schmid et al. |
| 2010/0256725 A1 | 10/2010 | Rasmussen |
| 2010/0292774 A1 | 11/2010 | Shalev |
| 2010/0318171 A1 | 12/2010 | Porter et al. |
| 2011/0093002 A1 | 4/2011 | Rucker et al. |
| 2011/0125251 A1 | 5/2011 | Cottone et al. |
| 2011/0208289 A1 | 8/2011 | Shalev |
| 2011/0208296 A1 | 8/2011 | Duffy et al. |
| 2011/0208297 A1 | 8/2011 | Tuval |
| 2011/0208298 A1 | 8/2011 | Tuval |
| 2011/0218607 A1 | 9/2011 | Arbefeuille et al. |
| 2011/0264184 A1 | 10/2011 | Heltai |
| 2011/0288622 A1 | 11/2011 | Chan et al. |

FOREIGN PATENT DOCUMENTS

| | | |
|---|---|---|
| EP | 1325716 A1 | 7/2003 |
| JP | 2002-253682 | 9/2002 |
| WO | 2004/017868 | 3/2004 |
| WO | 2005/002466 | 1/2005 |
| WO | 2005/037138 | 4/2005 |
| WO | 2005/041781 | 5/2005 |
| WO | 2005/041783 | 5/2005 |
| WO | 2006/007389 | 1/2006 |
| WO | 2006/028925 | 3/2006 |
| WO | 2006/070372 | 7/2006 |
| WO | 2007/084547 | 7/2007 |
| WO | 2007/144782 | 12/2007 |
| WO | 2008/008291 | 1/2008 |
| WO | 2008/035337 | 3/2008 |
| WO | 2008/042266 | 4/2008 |
| WO | 2008/047092 | 4/2008 |
| WO | 2008/047354 | 4/2008 |
| WO | 2008/053469 | 5/2008 |
| WO | 2008/107885 | 9/2008 |
| WO | 2008/140796 | 11/2008 |
| WO | 2009/078010 | 6/2009 |
| WO | 2009/116041 | 9/2009 |
| WO | 2009/116042 | 9/2009 |
| WO | 2009/118733 | 10/2009 |
| WO | 2010/024869 | 3/2010 |
| WO | 2010/024879 | 3/2010 |
| WO | 2010/031060 | 3/2010 |
| WO | 2010/045238 | 4/2010 |
| WO | 2010/062355 | 6/2010 |
| WO | 2010/088776 | 8/2010 |
| WO | 2010-128162 | 11/2010 |
| WO | 2010/150208 | 12/2010 |
| WO | 2011/004374 | 1/2011 |
| WO | 2011/007354 | 1/2011 |
| WO | 2011/055364 | 5/2011 |
| WO | 2011/064782 | 6/2011 |
| WO | 2011/067764 | 6/2011 |
| WO | 2011/070576 | 6/2011 |
| WO | 2011/080738 | 7/2011 |
| WO | 2011/095979 | 8/2011 |

(56) References Cited

FOREIGN PATENT DOCUMENTS

| WO | 2011/106532 | 9/2011 |
|----|-------------|--------|
| WO | 2011/106533 | 9/2011 |
| WO | 2011/106544 | 9/2011 |
| WO | 2012/049679 | 4/2012 |
| WO | 2012/104842 | 8/2012 |
| WO | 2012/111006 | 8/2012 |
| WO | 2012/117395 | 9/2012 |

OTHER PUBLICATIONS

An English Translation of an Office Action dated Aug. 25, 2011, which issued during the prosecution of Chinese Patent Application No. 200880014919.9.

Fonseca A et al., "Intravascular ultrasound assessment of the novel AngioSculpt scoring balloon catheter for the treatment of complex coronary lesions," J Invasive Cardiol 20(1):21-7 (Jan. 2008).

An International Search Report and a Written Opinion both dated Sep. 24, 2012, which issued during the prosecution of Applicant's PCT/IL2012/000060.

Khlif H et al., "Contribution to the Improvement of Textile Vascular Prostheses Crimping," Trends in Applied Sciences Research 6(9):1019-1027 (2011).

An International Search Report and a Written Opinion both dated Jul. 13, 2012, which issued during the prosecution of Applicant's PCT/IL2012/000083.

An International Search Report and a Written Opinion both dated Jul. 17, 2012, which issued during the prosecution of Applicant's PCT/IL2012/000095.

An International Search Report and a Written Opinion both dated Aug. 31, 2012, which issued during the prosecution of Applicant's PCT/IL2012/000148.

An International Search Report and a Written Opinion both dated Sep. 6, 2012, which issued during the prosecution of Applicant's PCT/IL2012/000190.

An International Search Report and a Written Opinion both dated Jun. 19, 2012, which issued during the prosecution of Applicant's PCT/IL2012/000241.

An International Search Report and a Written Opinion both dated Nov. 27, 2012, which issued during the prosecution of Applicant's PCT/IL2012/000300.

An International Search Report and a Written Opinion both dated Feb. 4, 2011, which issued during the prosecution of Applicant's PCT/IB2010/052861.

An International Search Report and a Written Opinion both dated Sep. 29, 2008, which issued during the prosecution of Applicant's PCT/IL08/000287.

An International Search Report and a Written Opinion both dated Mar. 11, 2009, which issued during the prosecution of Applicant's PCT/IL2007/001312.

An International Search Report and a Written Opinion both dated Jun. 30, 2009, which issued during the prosecution of Applicant's PCT/IL2008/001621.

An International Search Report and a Written Opinion both dated Nov. 5, 2010, which issued during the prosecution of Applicant's PCTIL2010000549.

An International Search Report and a Written Opinion both dated Dec. 3, 2010, which issued during the prosecution of Applicant's PCT/IL2010/000564.

An International Search Report and a Written Opinion both dated Mar. 10, 2011, which issued during the prosecution of Applicant's PCT/IL2010/000917.

An International Search Report and a Written Opinion both dated Aug. 4, 2011, which issued during the prosecution of Applicant's PCT/IL2010/000999.

An International Search Report and a Written Opinion both dated Mar. 30, 2011, which issued during the prosecution of Applicant's PCT/IL2010/001018.

An International Search Report and a Written Opinion both dated Apr. 18, 2011, which issued during the prosecution of Applicant's PCT/IL2010/001037.

An International Search Report and a Written Opinion both dated May 23, 2011, which issued during the prosecution of Applicant's PCT/IL2010/001087.

An International Search Report and a Written Opinion both dated Jun. 28, 2011, which issued during the prosecution of Applicant's PCT/IL2011/000135.

An International Search Report dated Oct. 4, 2012, which issued during the prosecution of Applicant's PCT/IL2012/000269.

An Office Action dated Apr. 27, 2011, which issued during the prosecution of U.S. Appl. No. 12/447,684.

An Office Action dated Nov. 12, 2010, which issued during the prosecution of U.S. Appl. No. 12/447,684.

An Office Action dated Mar. 24, 2011, which issued during the prosecution of U.S. Appl. No. 12/529,936.

An Office Action dated Oct. 28, 2011, which issued during the prosecution of U.S. Appl. No. 12/529,936.

An Office Action dated Jun. 19, 2012, which issued during the prosecution of U.S. Appl. No. 12/808,037.

An Office Action dated Oct. 11, 2012, which issued during the prosecution of U.S. Appl. No. 13/031,871.

An International Search Report and Written Opinion issued on Jun. 14, 2013 in PCT/IL2012/050506.

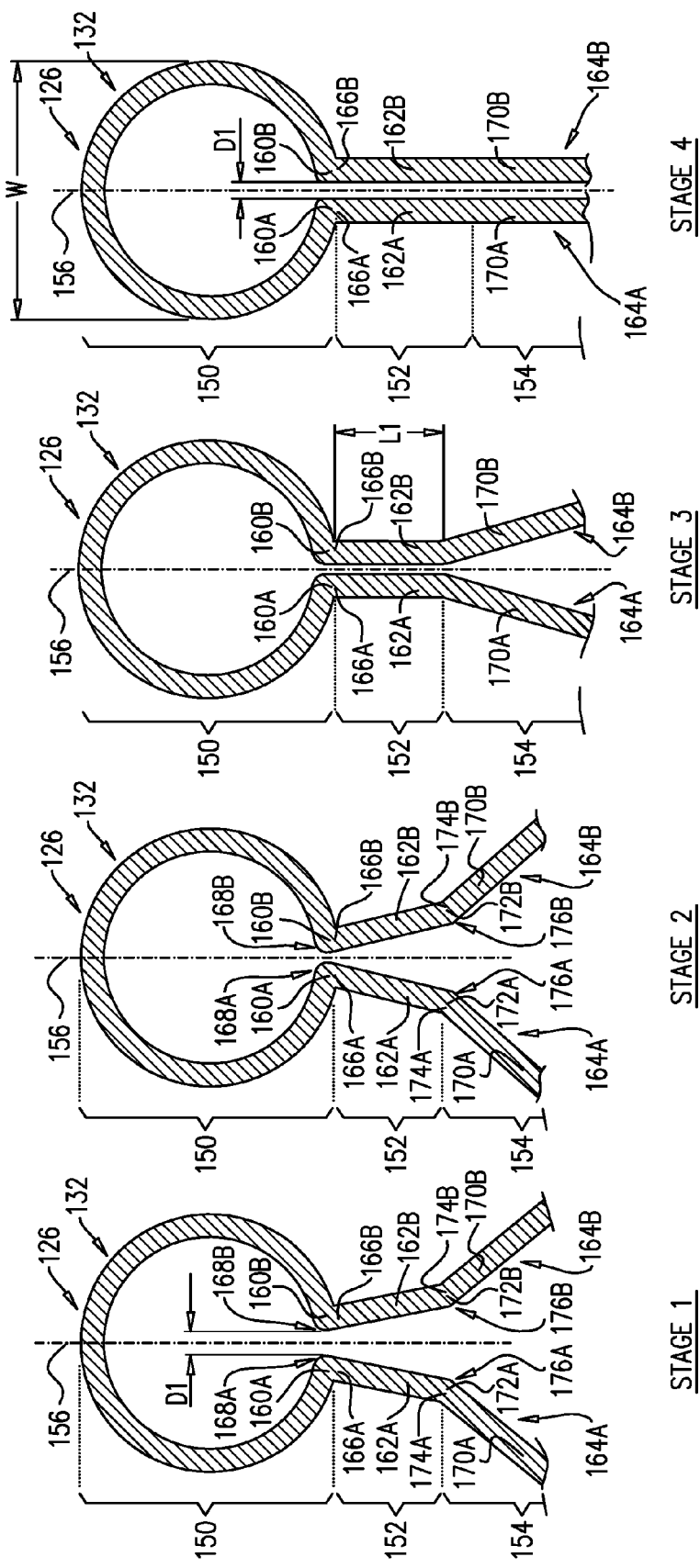

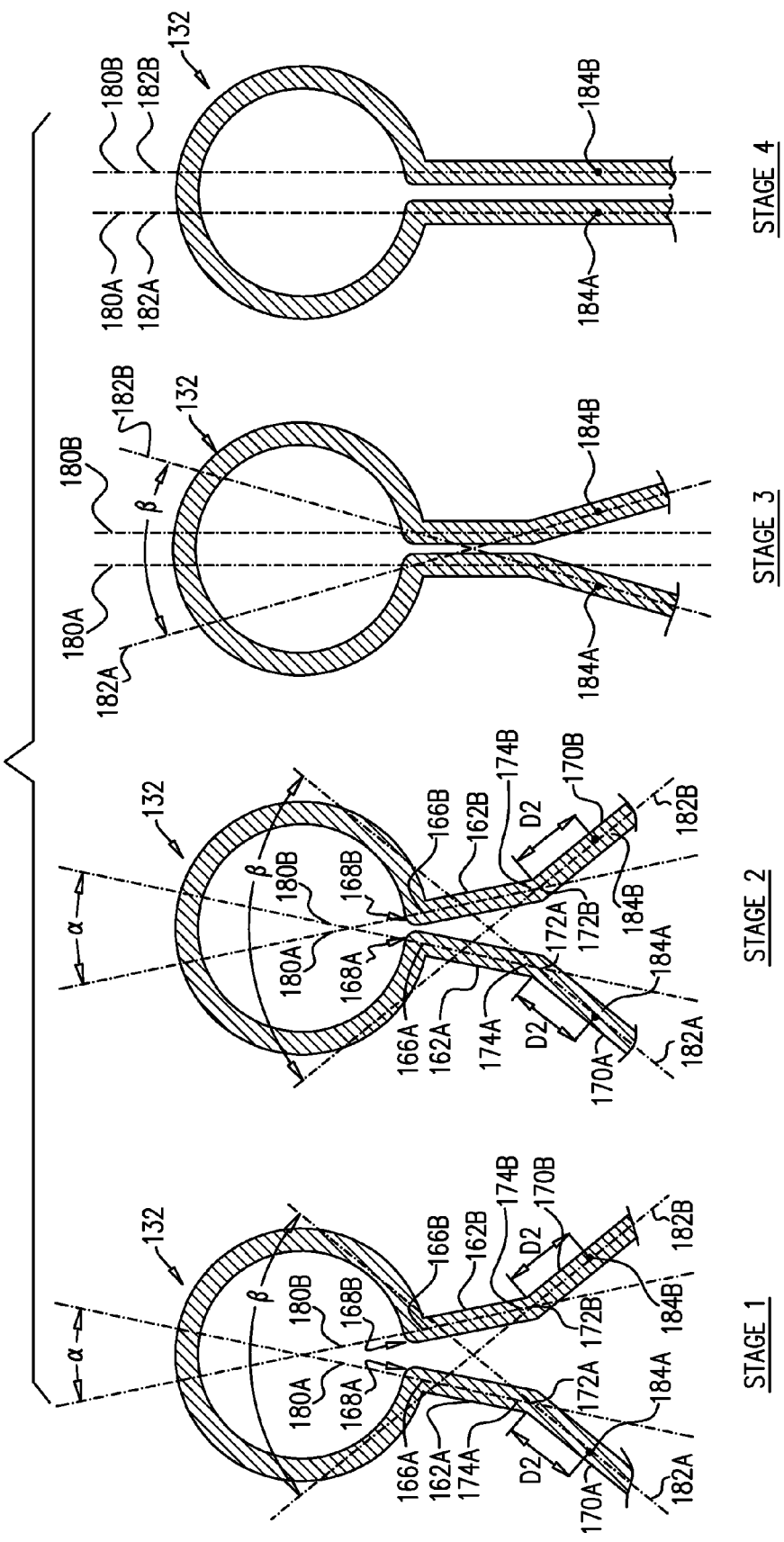

STENTS INCORPORATING A PLURALITY OF STRAIN-DISTRIBUTION LOCATIONS

CROSS-REFERENCE TO RELATED APPLICATIONS

The present application claims the benefit of U.S. Provisional Patent Application 61/496,613, filed Jun. 14, 2011, which is assigned to the assignee of the present application and is incorporated herein by reference.

FIELD OF THE APPLICATION

The present application relates generally to prostheses, and specifically to tubular prostheses, including endovascular grafts and stent-grafts.

BACKGROUND OF THE APPLICATION

Endovascular prostheses are sometimes used to treat aortic aneurysms. Such treatment includes implanting a stent or stent-graft within the diseased vessel to bypass the anomaly. An aneurysm is a sac formed by the dilation of the wall of the artery. Aneurysms may be congenital, but are usually caused by disease or, occasionally, by trauma. Aortic aneurysms which commonly form between the renal arteries and the iliac arteries are referred to as abdominal aortic aneurysms ("AAAs"). Other aneurysms occur in the aorta, such as thoracic aortic aneurysms ("TAAs") and aortic uni-iliac ("AUI") aneurysms.

SUMMARY OF APPLICATIONS

In some applications of the present invention, an endovascular system is provided that comprises a stent and, typically, a graft member that at least partially covers the stent. The stent comprises a plurality of circumferential bands disposed about a longitudinal axis of the stent, each of which bands comprises a plurality of struts connected to one another. At least one of the circumferential bands is shaped so as to define a plurality of distally-directed peaks alternating with a plurality of proximally-directed troughs, and one or more strain-concentration modules. As the stent is compressed for placement in a catheter for delivery to a site in a body of a subject, the stent typically transitions from a radially-expanded state, through a plurality of partially radially-compressed states, to a radially-compressed state. The strain-concentration modules are configured such that as the stent is radially compressed, the resulting strain on the stent is typically accumulated in at least three phases of the compression at different locations of the strain-concentration modules. Such distribution of stress helps prevent plastic (non-elastic) deformation of the stent when the stent is radially compressed, which could cause the stent not to return to its original shape upon subsequent radial expansion during implantation. This stress distribution may be particularly important in stents that are highly compressed to provide a highly reduced crossing profile for percutaneous delivery.

Each of the strain-concentration modules comprises an open loop section, a primary neck section, and a secondary section, and has a central axis parallel to the longitudinal axis of the stent. The open loop section comprises one of the distally-directed peaks, and is shaped so as to define two open loop ends disposed on opposite sides of the central axis. The open loop section has a greatest outer width measured perpendicular to the central axis when the stent is in its radially-compressed state. Typically, a first distance between the open loop ends is less than 30%, such as less than 20%, of the greatest outer width when the stent is in its radially-compressed state.

The primary neck section comprises two primary segments of two of the struts, respectively, disposed on opposite sides of the central axis. Distal ends of the primary segments are connected to the two proximal open loop ends, respectively, at respective primary junctions. Typically, each of the primary segments has a length equal to at least 33% of the greatest outer width of the open loop section. The secondary section comprises two secondary segments of the two of the struts, respectively, disposed on opposite sides of the central axis. Distal ends the secondary segments, respectively, are connected to proximal ends of the primary segments, respectively, at respective secondary junctions.

The primary segments define primary straight lines, respectively, which pass through the distal and proximal ends the primary segments, respectively. The primary lines define a primary angle with each other. Similarly, the secondary segments define secondary straight lines, respectively, which pass through (i) the distal ends of the secondary segments, respectively, and (ii) points on the secondary segments at a second distance from the distal ends of the secondary segments, respectively, which second distance equals 25% of the greatest outer width of the open loop section. The secondary lines define a secondary angle with each other.

When the stent is in its radially-compressed state, the primary angle typically has a compressed value of between 0 and 5 degrees, and the secondary angle typically has a compressed value of between 0 and 5 degrees. When the stent is in its radially-expanded state, the primary angle typically has an expanded value that is greater than the compressed value of the primary angle, and the secondary angle typically has an expanded value that is greater than the expanded value of primary angle. When the stent is in at least one of its partially radially-compressed states, the primary angle typically has a partially-compressed value of between 0 and 10 degrees, and the secondary angle typically has a partially-compressed value that is greater than the partially-compressed value of the primary angle.

As mentioned above, as the stent is radially compressed, the resulting strain on the stent is typically accumulated in at least three phases of the compression. In the first phase, as the stent transitions from its radially-expanded state to one of the partially radially-compressed states, the strain is primarily accumulated in the open loop section itself, until the open loop ends come together. In the second, subsequent phase, as the stent transitions to another of the radially-compressed states, the strain is primarily accumulated at the primary junctions, i.e., at the interfaces between the open loop section and the primary neck section, until the primary segments of the primary neck segment come together. In the third, subsequent phase, as the stent transitions from the partially radially-compressed states to the radially-compressed state, the strain is primarily accumulated at the secondary junctions (below the primary neck section), i.e., at the interfaces between the primary neck segment and the secondary section. The primary neck section typically creates a buffer zone that allows the strain accumulated in the loop to have less effect on the strain along the loop and the open loop ends, which ends constitute pivot points for the bending of the primary segments attached thereto.

There is therefore provided, in accordance with an application of the present invention, apparatus including a stent (120) having proximal and distal ends (140, 142), which is configured to assume radially-compressed and radially-expanded states, and which includes a plurality of circumferential bands (122) disposed about a longitudinal axis (123) of the stent (120), each of which bands (122) includes a plurality of struts (124) connected to one another, wherein at least one of the bands (122) is shaped so as to define a plurality of distally-directed peaks (126) alternating with a plurality of proximally-directed troughs (128), and one or more strain-concentration modules (132), each of which modules (132) has a central axis (156) parallel to the longitudinal axis (123) of the stent (120), and includes:

an open loop section (150), which (a) includes one of the distally-directed peaks (126), and (b) is shaped so as to define first and second proximal open loop ends (160A, 160B) disposed on opposite sides of the central axis (156), wherein, when the stent (120) is in its radially-compressed state, the open loop section (150) has a greatest outer width (W) measured perpendicular to the central axis (156), and a first distance (D1) between the first and the second proximal open loop ends (160A, 160B) is less than 20% of the greatest outer width (W);

a primary neck section (152), which includes first and second primary segments (162A, 162B) of first and second ones of the struts (164A, 164B), respectively, disposed on opposite sides of the central axis (156), wherein first and second distal ends (166A, 166B) of the first and the second primary segments (162A, 162B) are connected to the first and the second proximal open loop ends (160A, 160B) at first and second primary junctions (168A, 168B), respectively, and wherein each of the first and the second primary segments (162A, 162B) has a length (L1) equal to at least 33% of the greatest outer width (W) of the open loop section (150); and a secondary section (154), which includes first and second secondary segments (170A, 170B) of the first and the second struts (164A, 164B), respectively, disposed on opposite sides of the central axis (156), wherein first and second distal ends (172A, 172B) of the first and the second secondary segments (170A, 170B), respectively, are connected to first and second proximal ends (174A, 174B) of the first and the second primary segments (170A, 170B) at first and second secondary junctions (176A, 176B), respectively, wherein the first primary segment (162A) defines a first primary straight line (180A), which passes through the first distal end (166A) and the first proximal end (174A) of the first primary segment (162A), and the second primary segment (162B) defines a second primary straight line (180B), which passes through the second distal end (166B) and the second proximal end (174B) of the second primary segment (162B), wherein the first primary line (180A) defines a distal-facing primary angle ($\alpha$) with the second primary line (180B) which (i) has a compressed value of between 0 and 5 degrees, when the stent (120) is in its radially-compressed state, and (ii) has an expanded value that is between (x) 5 degrees greater than the compressed value of the primary angle ($\alpha$) and (y) 60 degrees, when the stent (120) is in its radially-expanded state, wherein the first secondary segment (170A) defines a first secondary straight line (182A), which passes through (i) the first distal end (172A) of the first secondary segment (170A) and (ii) a first point (184A) on the first secondary segment (170A) at a second distance (D2) from the first distal end (172A) of the first secondary segment (170A), and the second secondary segment (170B) defines a second secondary straight line (182B), which passes through (i) the second distal end (172B) of the second secondary segment (170B) and (ii) a second point (184B) on the second secondary segment (170B) at the second distance (D2) from the second distal end (172B) of the second secondary segment (170B), which second distance (D2) equals 25% of the greatest outer width (W), and wherein the first secondary line (182A) defines a distal-facing secondary angle ($\beta$) with the second secondary line (182B) which (i) has a compressed value of between 0 and 5 degrees, when the stent (120) is in its radially-compressed state, and (ii) has an expanded value that is greater than the expanded value of the primary angle ($\alpha$), when the stent (120) is in its radially-expanded state.

For some applications, the expanded value of the secondary angle ($\beta$) is between (x) 5 degrees greater than the expanded value of the primary angle ($\alpha$) and (y) 90 degrees.

For some applications, radii of curvature of the first and the second struts (164A, 164B) at the first and the second secondary junctions (176A, 176B), respectively, are less than 50% of a length of the first primary segment (162A) and 50% of a length of the second primary segment (162B), respectively, when the stent (120) is in its radially-expanded state.

For some applications, the stent (120) is configured to assume a plurality of partially radially-compressed states between its radially-compressed and its radially-expanded states, and wherein, when the stent (120) is in at least one of its partially radially-compressed states, the primary angle ($\alpha$) has a partially-compressed value of between 0 and 10 degrees, and the secondary angle ($\beta$) has a partially-compressed value that is greater than the partially-compressed value of the primary angle ($\alpha$).

For some applications, none of the struts (124), other than the first and the second struts (164A, 164B), is connected to the first primary junction (168A) or the second primary junction (168B). Alternatively or additionally, for some applications, none of the struts (124), other than the first and the second struts (164A, 164B), is connected to the first secondary junction (176A) or the second secondary junction (176B).

For some applications, the first and the second primary segments (162A, 162B) of the primary neck section (152) are straight when the stent (120) is in its radially-compressed state. Alternatively or additionally, for some applications, the first and the second primary segments (162A, 162B) of the primary neck section (152) are straight when the stent (120) is in its radially-expanded state.

For some applications, the first and the second primary segments (162A, 162B) of the primary neck section (152) are curved when the stent (120) is in its radially-expanded state, and are straight when the stent (120) is in its radially-compressed state. Alternatively or additionally, for some applications, the stent (120) is shaped so as to generally define a cylinder when in its radially-expanded state, and the struts (124) of the strain-concentration modules (132) coincide with a surface of the cylinder.

For some applications, the at least one of the bands (122) is serpentine at least when the stent (120) is in its radially-expanded state. For some applications, the at least one of the bands (122) extends around an entire circumference of the stent (120). For some applications, a length of the open loop section, measured along a perimeter thereof, is at least 0.7 mm.

For some applications, first and second proximal ends (174A, 174B) of the first and second secondary segments (170A, 170B), respectively, are directly or indirectly connected to another one of the bands (122).

For any of the applications described above:

the secondary section (154) may be a secondary neck section (154), each of the first and second secondary segments (170A, 170B) may have a length equal to at least 66% of the greatest outer width (W) of the open loop section (150), each of the one or more strain concentration modules (132) may further include a tertiary section (200), which includes first and second tertiary segments (202A, 202B) of the first and the second struts (164A, 164B), respectively, disposed on opposite sides of the central axis (156), wherein first and second distal ends (204A, 204B) of the first and the second tertiary segments (202A, 202B), respectively, are connected to first and second proximal ends (206A, 206B) of the first and the second secondary segments (170A, 170B) at first and second tertiary junctions (208A, 208B), respectively, the first tertiary segment (202A) may define a first tertiary straight line (210A), which passes through (i) the first distal end (204A) of the first tertiary segment (202A) and (ii) a third point (212A) on the first tertiary segment (202A) at the second distance (D2) from the first distal end (204A) of the first tertiary segment (202A), and the second tertiary segment (202B) defines a second tertiary straight line (210B), which passes through (i) the second distal end (204B) of the second tertiary segment (202B) and (ii) a fourth point (212B) on the second tertiary segment (202B) at the second distance (D2) from the second distal end (204B) of the second tertiary segment (202B), and the first tertiary line (210A) may define a tertiary angle (θ) with the second tertiary line (210B) which (i) has a compressed value of at least 105% of the compressed value of angle β (beta), when the stent is in its radially-compressed state, and (ii) has an expanded value that is between (x) 120% of the expanded value of the secondary angle (β) and (y) 135 degrees, when the stent (120) is in its radially-expanded state.

For some applications, the first and the second secondary segments (170A, 170B) of the secondary neck section (154) are straight when the stent (120) is in its radially-compressed state. Alternatively or additionally, for some applications, the first and the second secondary segments (170A, 170B) of the secondary neck section (154) are straight when the stent (120) is in its radially-expanded state.

For any of the applications described above, the stent (120) may include a metal. For example, the metal may include a superelastic alloy, such as Nitinol.

For any of the applications described above, the stent (120) may be self-expanding from the radially-compressed state to the radially-expanded state.

For any of the applications described above, the radially-expanded relaxed state of the stent (120) may be achieved by heat-setting of the stent (120) in the radially-expanded state that is more radially expanded than an initial as-cut state of the stent (120).

For any of the applications described above, the circumferential bands (122) may include a plurality of substantially M-shaped segments.

For any of the applications described above, the circumferential bands (122) may be adjacently connected therebetween.

For any of the applications described above, the apparatus may further include a graft member (30), which covers at least a portion of the stent (120) and is securely connected thereto.

The present invention will be more fully understood from the following detailed description of embodiments thereof, taken together with the drawings, in which:

BRIEF DESCRIPTION OF THE DRAWINGS

FIGS. 5A-B are schematic illustrations of a single strain-concentration module of a stent of the endovascular system of FIG. 4, in four radial-expansion states, in accordance with an application of the present invention;

DETAILED DESCRIPTION OF APPLICATIONS

Figure 1:
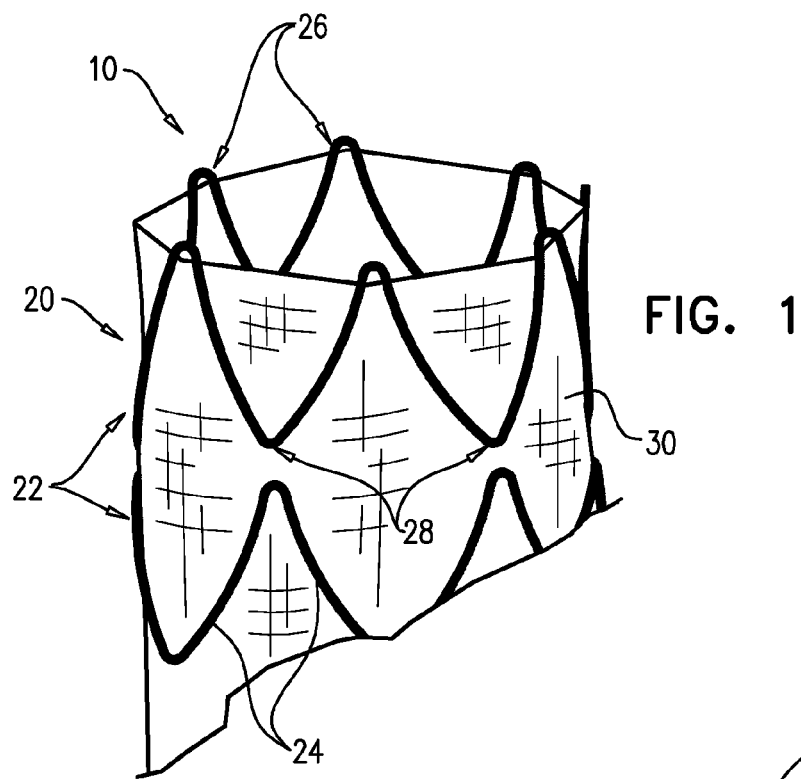
FIG. 1 is a schematic illustration of an endovascular system, in accordance with an application of the present invention.

FIG. 1 is a schematic illustration of an endovascular system 10, in accordance with an application of the present invention. System 10 comprises a stent 20, which comprises a plurality of circumferential bands 22 disposed about a longitudinal axis of the stent, each of which bands comprises a plurality of struts 24 connected to one another. Stent 20 is shown in FIG. 1 in a radially-expanded state. In the illustrated configuration, each of circumferential bands 22 comprises a plurality of M-shaped segments, which are shaped so as to define distally-directed turns (peaks) 26 and proximally-directed turns (troughs) 28. System 10 further comprises a graft member 30, which covers at least a portion of stent 20 (either inside the stent, as shown, or outside the stent) and is securely connected thereto. In the configuration shown in FIG. 1, circumferential bands 22 are not directly connected to one another, but instead are indirectly connected by graft member 30, to form stent 20.

Figure 2:
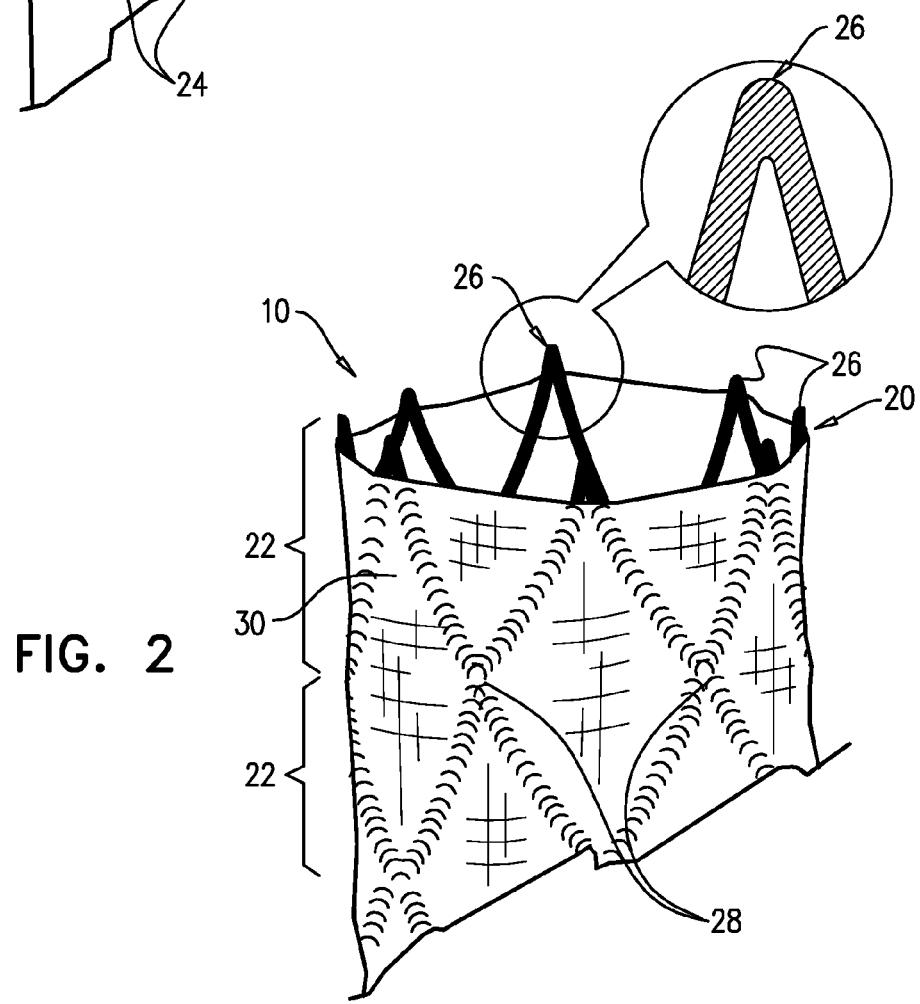
FIG. 2 is a schematic illustration another configuration of the endovascular system of FIG. 1, in accordance with an application of the present invention.

FIG. 2 is a schematic illustration another configuration of endovascular system 10, in accordance with an application of the present invention. Stent 20 is shown in FIG. 2 in a radially-expanded state. In the configuration shown in FIG. 2, circumferential bands 22 are coupled to one another along the longitudinal axis of stent 20. In addition, graft member 30 is disposed outside of stent 20. The blow-up in FIG. 2 shows an enlargement of a single one of distally-directed peaks 26. Of all portions of stent 20, peaks 26 and troughs 28 are subjected to the greatest amount of strain as stent 20 is crimped from a radially-expanded state (as shown in FIG. 2) to a radially-compressed state (not shown in FIG. 2).

Figure 3:
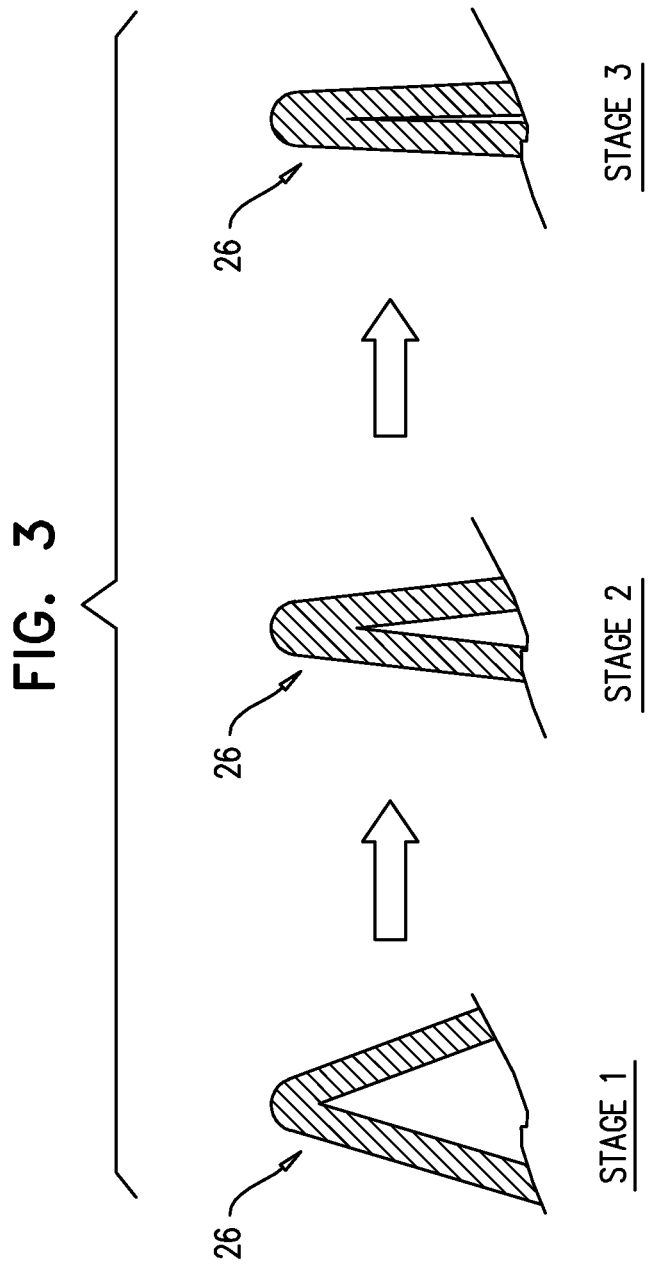
FIG. 3 is a schematic illustration of a single peak of a stent of the endovascular system of FIG. 2, in three radial-expansion states, in accordance with an application of the present invention.

FIG. 3 is a schematic illustration of a single one of peaks 26 of stent 20 of FIG. 2, in three radial-expansion states, in accordance with an application of the present invention. Stage 1 is a radially-expanded state, as shown in FIG. 2. Stage 2 is an intermediate state, in which the stent is partially radially-compressed. Stage 3 is a radially-compressed state. In this latter state, peak 26 is subjected to the maximal amount of strain, as strain increases with increased radial compression of the stent. Stent 20 typically transitions from Stage 1 to Stage 2 to Stage 3, through additional intermediary states between these stages, as stent 20 is compressed from its relaxed, radially-expanded state to its radially-compressed state, for placement in a catheter for delivery to a site in a body of a subject.

Figure 4:
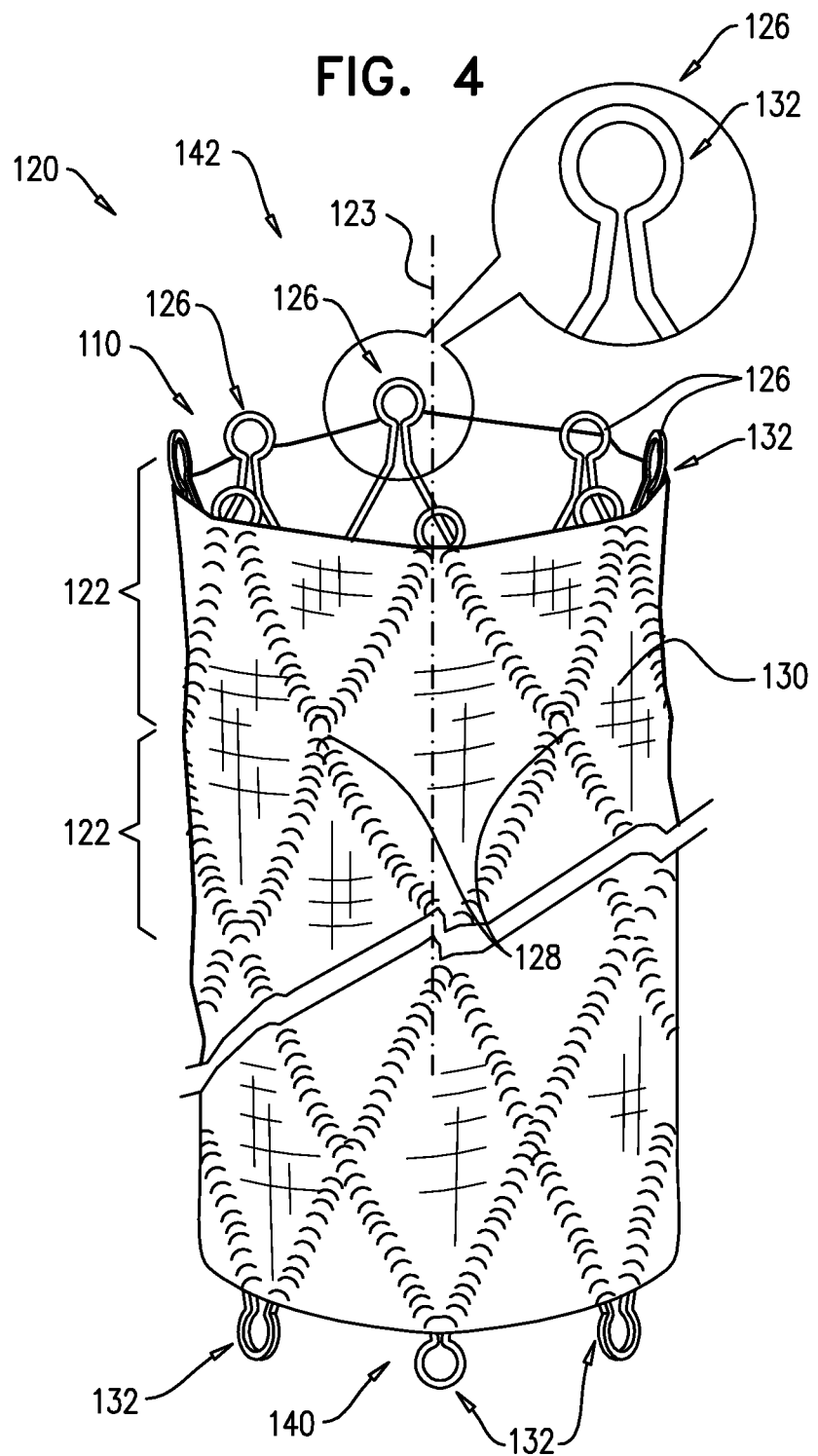
FIG. 4 is a schematic illustration of another endovascular system, in accordance with an application of the present invention.

FIG. 4 is a schematic illustration of an endovascular system 110, in accordance with an application of the present invention. System 110 comprises a stent 120, which comprises a plurality of circumferential bands 122 disposed about a longitudinal axis 123 of the stent, each of which bands comprises a plurality of struts 124 connected to one another. Circumferential bands 122 together define a fluid flow path longitudinally therethrough. Stent 120 is shown in FIG. 4 in a radially-expanded state. For some applications, one or more (e.g., all) of the bands are serpentine at least when the stent is in its radially-expanded state. System 110 typically further comprises a graft member 130, which covers at least a portion of stent 20 (either outside the stent, as shown, or inside the stent) and is securely connected thereto. In the configuration shown in FIG. 4, circumferential bands 122 are directly adjacently connected to one another along longitudinal axis 123. Alternatively, circumferential bands 122 may be indirectly connected by graft member 130, such as shown in FIG. 1. Typically, one or more (e.g., all) of bands 122 extends around an entire circumference of stent 120. For some applications, stent 120 comprises a metal, such as a superelastic alloy, e.g., Nitinol.

At least one (e.g., at least two, or all) of circumferential bands 122 is shaped so as to define a plurality of distally-directed turns (peaks) 126 alternating with a plurality of proximally-directed turns (troughs) 128. For some applications, each of circumferential bands 122 comprises a plurality of M-shaped segments, which are shaped so as to define peaks 126 and troughs 128. The blow-up in FIG. 4 shows an enlargement of a single strain-concentration module 132, as described hereinbelow with reference to FIGS. 5A-B. Stent 120 has proximal and distal ends 140 and 142. Typically, stent 120 is shaped so as to generally define a cylinder when in its radially-expanded state, as shown in FIG. 4, and struts 124 of strain-concentration modules 132 coincide with a surface of the cylinder. For the sake of clarity, the various geometric features of strain-concentration module 132 are described hereinbelow, and recited in the claims, as though the struts fall within a single plane; in actual practice, the struts generally coincide with the surface of a cylinder.

FIGS. 5A-B are schematic illustrations of a single one of strain-concentration modules 132 of stent 120, in four radial-expansion states, in accordance with an application of the present invention. FIGS. 5A and 5B are identical, except that for clarity of illustration, the reference numerals are distributed between the two figures. Stage 1 is a radially-expanded state, as shown in FIG. 4. Stages 2 and 3 are intermediate states, in which the stent is partially radially-compressed. (Stent 120 assumes a plurality (generally an infinite number) of partially radially-compressed states between the radially-expanded and radially-compressed states; Stages 2 and 3 are two of these intermediary states.) Stage 4 is a radially-compressed state. In this latter state, peak 126 is subjected to the maximal amount of strain, as strain increases with increased radial compression of the stent. Stent 120 typically transitions from Stage 1 to Stage 4, through intermediary states between these stages, including Stages 2 and 3, as stent 120 is compressed from its relaxed, radially-expanded state to the radially-compressed state, for placement in a catheter for delivery to a site in a body of a subject.

As labeled in FIG. 5A, each of strain-concentration modules 132 comprises an open loop section 150, a primary neck section 152, and a secondary section 154, and has a central axis 156 parallel to longitudinal axis 123 of the stent 120 (shown in FIG. 4), configured as follows:

Open loop section 150 comprises one of distally-directed peaks 126. Open loop section 150 is shaped so as to define first and second proximal open loop ends 160A and 160B disposed on opposite sides of central axis 156. Open loop section 150 has a greatest outer width W measured perpendicular to central axis 156 when stent 120 is in its radially-compressed state (as used herein, including in the claims, greatest outer width W is always measured when the stent is in its radially-compressed state). For some applications, a length of open loop section 150, measured along a perimeter thereof, is at least 0.7 mm, no more than 4 mm, and/or between 0.7 and 4 mm. For some applications, open loop section 150 is symmetrical about central axis 156 (as shown), while for other applications, the open loop section is not symmetrical about the central axis (not shown). Alternatively, as described below, open loop section 150 comprises one of proximally-directed troughs 128, instead of one of distally-directed peaks 126. In this case, references hereinbelow to "proximal" are to be understood as "distal," and vice versa.

Primary neck section 152 comprises first and second primary segments 162A and 162B of first and second struts 164A and 164B, respectively, disposed on opposite sides of central axis 156. First and second distal ends 166A and 166B of first and second primary segments 162A and 162B are connected to first and second proximal open loop ends 160A and 160B at first and second primary junctions 168A and 168B, respectively. Typically, each of first and second primary segments 162A and 162B has a length L1 (labeled in Stage 3 of FIG. 5A) equal to at least 33% of greatest outer width W of open loop section 150, no more than 50% of W, and/or between 33% and 50% of W. For some applications, primary neck section 152 is symmetrical about central axis 156 (as shown), while for other applications, the primary neck section is not symmetrical about the central axis (not shown).

Secondary section 154 comprises first and second secondary segments 170A and 170B of first and second struts 164A and 164B, respectively, disposed on opposite sides of central axis 156. First and second distal ends 172A and 172B of first and second secondary segments 170A and 170B, respectively, are connected to first and second proximal ends 174A and 174B of first and second primary segments 162A and 162B at first and second secondary junctions 176A and 176B, respectively. For some applications, secondary section 154 is symmetrical about central axis 156 (as shown), while for other applications, the secondary neck section is not symmetrical about the central axis (not shown).

For some applications, strain-concentration module 132 is symmetrical about central axis 156 (as shown), while for other applications, the strain-concentration module is not symmetrical about the central axis (not shown).

Figure 9:
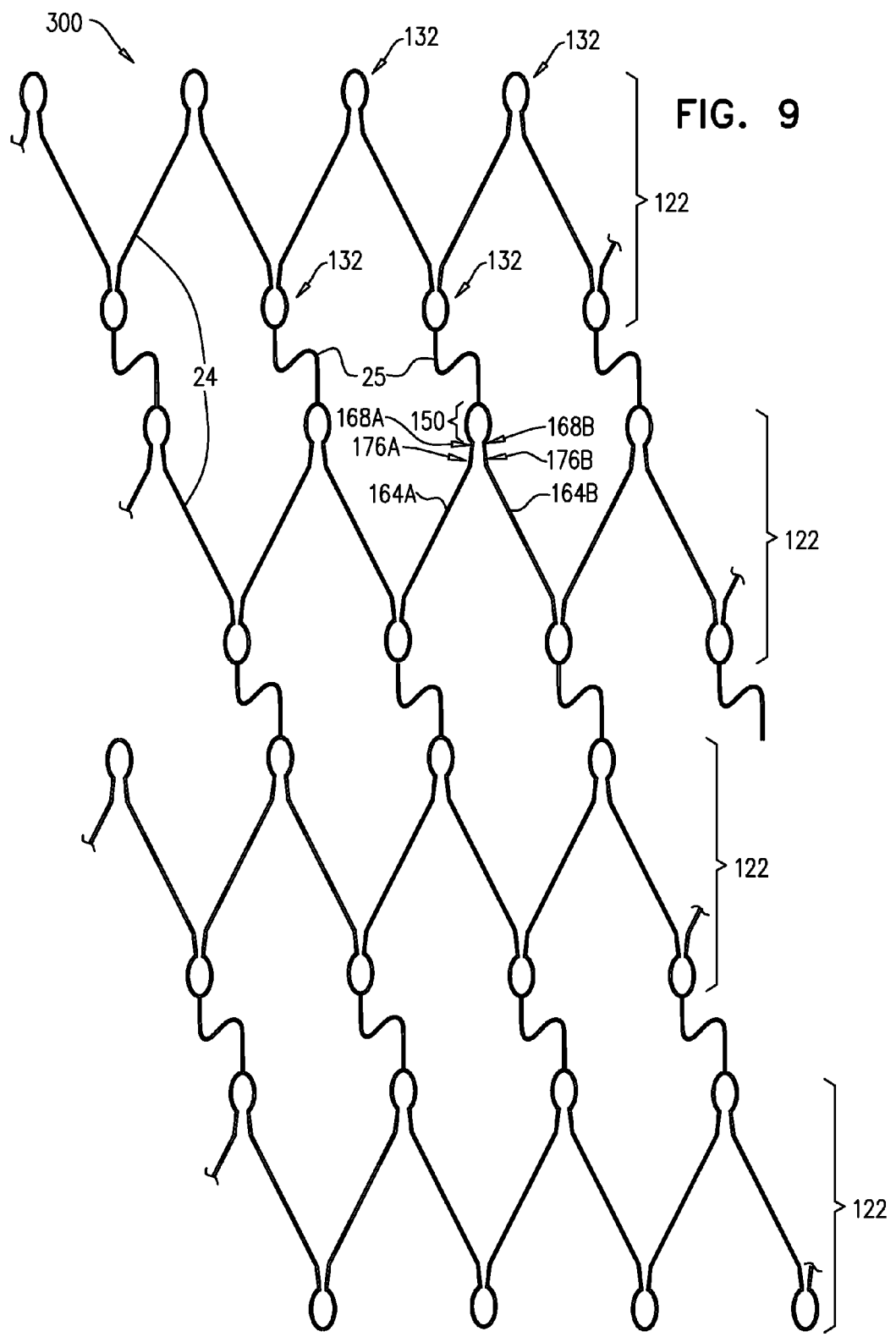
FIG. 9 is a schematic planar projection of a stent pattern, in accordance with an application of the present invention.

For some applications, such as shown in FIGS. 4 and 9, stent 120 is shaped so as to define additional strain-concentration modules 132, open loops sections 150 of which comprise respective ones of proximally-directed troughs 128. It is noted that "proximal" and "distal" are used in the present application, including in the claims, as relative, rather than absolute, directional terms.

Typically, when the stent is in its radially-compressed state (Stage 4), and a portion of its intermediary states (including Stages 2 and 3), a first distance D1 between first and second proximal open loop ends 160A and 160B is less than 30%, such as less than 20% (e.g., less than 10%, or less than 5%), of greatest outer width W (measured when the stent is in its radially-compressed state). For some applications, first distance D1 equals 0, i.e., first and second proximal open loop ends 160A and 160B touch each other when the stent is in its radially-compressed state (Stage 4), and in a portion of its intermediary states (including Stages 2 and 3). Alternatively, first and second proximal loop ends 160A and 160B remain a slight distance (first distance D1) apart, such as if graft member 30 intervenes. Alternatively or additionally, an angle subtended by an arc between first and second loop ends 160A and 160B is less than 20 degrees, e.g., 0 degrees, when the stent is in its radially-compressed state (Stage 4), and a portion of its intermediary states (including Stages 2 and 3).

Typically, first distance D1 greater when the stent is in its radially-expanded state (Stage 1) than when the stent is in its radially-compressed state (Stage 4); for example, the difference between D1 in these two states may be equal to at least 30% of the value of D1 when the stent is in its radially-expanded state. Alternatively or additionally, an angle subtended by an arc between first and second loop ends 160A and 160B is greater when the stent is in its radially-expanded state (Stage 1) than when the stent is in its radially-compressed state (Stage 4); for example, the difference between the angle in these two states may be at least 20% of the value of the angle when the stent is in its radially-expanded state.

As labeled in FIG. 5B, first primary segment 162A defines a first primary straight line 180A that passes through first distal end 166A and first proximal end 174A of first primary segment 162A, and second primary segment 162B defines a second primary straight line 180B that passes through second distal end 166B and second proximal end 174B of second primary segment 162B. First primary line 180A defines a distal-facing primary angle α (alpha) with second primary line 180B (and a proximal-facing primary angle having a value equal to that of angle α (alpha)). Similarly, first secondary segment 170A defines a first secondary straight line 182A, which passes through (i) first distal end 172A of first secondary segment 170A and (ii) a first point 184A on first secondary segment 170A at a second distance D2 from first distal end 172A of first secondary segment 170A, and second secondary segment 170B defines a second secondary straight line 182B that passes through (i) second distal end 172B of second secondary segment 170B and (ii) a second point 184B on second secondary segment 170B at second distance D2 from second distal end 172B of second secondary segment 170B. Second distance D2 equals 25% of greatest outer width W. (First and second secondary lines 182A and 182B may thus be considered approximate representations of a longitudinal axis of first and second secondary segments 170A and 170B, respectively, in respective vicinities of first and second distal ends 172A and 172B.) First secondary line 182A defines a distal-facing secondary angle β (beta) with second secondary straight line 182B (and a proximal-facing secondary angle having a value equal to that of angle β (beta)). (Points 184A and 184B are geometrical reference points, which are typically not actually marked on stent 120.)

As mentioned above, Stages 1, 2, 3, and 4 represent three consecutively increasing levels of compression of stent 120. Stent 120 is typically configured such that:

when the stent is in Stage 4, its radially-compressed state, typically (a) primary angle α (alpha) has a compressed value of between 0 and 5 degrees, e.g., 0 degrees, as labeled in FIG. 5B, and (b) secondary angle β (beta) has a compressed value of between 0 and 5 degrees, or between 3 and 20 degrees, and/or greater than the compressed value of primary angle α (alpha). (When the values equal 0 degrees, the lines are parallel, i.e., can be considered to intersect at infinity.)

when the stent is in Stage 3, a state of partial radial compression, typically (a) primary angle α (alpha) has a partially-compressed value of between and 10 degrees, e.g., 0 degrees, as labeled in FIG. 5B, and (b) secondary angle β (beta) has a partially-compressed value that is (i) greater than the partially-compressed value of primary angle α (alpha), such as at least 5 degrees, e.g., at least degrees, greater than the partially-compressed value of primary angle α (alpha), and/or (ii) at least 5 degrees, less than 90 degrees, e.g., less than 60 degrees, such as less than 20 degrees, and/or between 5 and 90 degrees, e.g., between 5 and 20 degrees. It is noted that, as mentioned above, stent 120 assumes a plurality of partially radially-compressed states; the above-mentioned properties apply to at least one of these states, and generally to many of these states.

when the stent is in Stage 1, its radially-expanded state, and Stage 2, another state of partial radial compression, typically (a) primary angle α (alpha) has an expanded value that is (i) greater than the compressed value of primary angle α (alpha), such as at least 5 degrees greater than the compressed value of primary angle α (alpha), and/or (ii) at least 5 degrees, less than 90 degrees, such as less than 60 degrees, and/or between 5 and 90 degrees, e.g., between 5 and 60 degrees, and (b) secondary angle β (beta) has an expanded value that is (i) greater than the expanded value of primary angle α (alpha), such as at least 5 degrees greater than the expanded value of primary angle α (alpha), and/or (ii) at least 10 degrees, less than 120 degrees, e.g., less than 90 degrees, and/or between 10 and 120 degrees, e.g., between 10 and 90 degrees.

Stage 2 is more radially compressed than Stage 1 primarily because first distance D1, described above, is less in Stage 2 than in Stage 1. In addition, primary angle α (alpha) and secondary angle β (beta) may each be slightly less in Stage 2 than in Stage 1.

For some applications, radii of curvature of first and second struts 164A and 164B at first and second secondary junctions 176A and 176B, respectively, are less than 50% (e.g., less than 25%) of a length of first primary segment 162A and 50% (e.g., less than 25%) of a length of second primary segment 162B, respectively, when the stent is in its radially-expanded state (Stage 1) and/or in at least a portion of its partially radially-compressed states (Stage 2 and/or 3). For example, one or both of the radii of curvature may be equal to 0 (i.e., first and/or second secondary junctions 176A and 176B may define respective corners), such as shown in FIGS. 5A-B, 6, and 7.

As stent 120 is radially compressed (such as by crimping), the resulting strain on the stent is typically accumulated in at least three phases of the compression. In the first phase, as the stent transitions from Stage 1 to Stage 2, the strain is primarily accumulated in open loop section 150 itself, until first and second proximal open loop ends 160A and 160B come together. (When these loop ends come together, they optionally touch one another, or remain a slight distance (first distance D1) apart, such as if graft member 30 intervenes, such as described above.)

In the second, subsequent phase, as the stent transitions from Stage 2 to Stage 3, the strain is primarily accumulated at first and second primary junctions 168A and 168B, i.e., at the interfaces between open loop section 150 and primary neck segment 152, until first and second primary segments 162A and 162B of primary neck segment 152 come together. (When the primary segments come together, they optionally touch one another, or remain a slight distance (first distance D1) apart, such as if graft member 30 intervenes.)

In the third, subsequent phase, as the stent transitions from Stage 3 to Stage 4, the strain is primarily accumulated at first and second secondary junctions 176A and 176B (below primary neck section 152), i.e., at the interfaces between primary neck segment 152 and secondary section 154. Primary neck section 152 typically creates a buffer zone that allows the strain accumulated in the loop to have less effect on the strain along the loop and the open loop ends, which ends constitute pivot points for the bending of the primary segments attached thereto.

Such distribution of stress helps prevent plastic (non-elastic) deformation of stent 120 when the stent is radially compressed, which could cause the stent not to return to its original shape upon subsequent radial expansion during implantation. This stress distribution may be particularly important in stents that are highly compressed (e.g., crimped) to provide a highly reduced crossing profile for percutaneous delivery. The configurations of stent 20 shown in FIGS. 1-3 generally do not provide such effective stress distribution, which may result in plastic deformation if stent 20 is highly radially compressed. Typically, stent 120 is self-expanding from the radially-compressed state to the radially-expanded state, via the states of intermediary compression, such upon release of the stent from a delivery tool.

For some applications, as shown in FIGS. 5A-B, first and second primary segments 162A and 162B of primary neck section 152 are straight when stent 120 is in its radially-compressed state (Stage 4), when stent 120 is in its radially-expanded state (Stage 1), and/or when stent 120 is in a partially-compressed state (such as Stages 2 and/or 3). For some applications, as shown in FIGS. 5A-B, respective portions of first and second secondary segments 170A and 170B of secondary section 154, between first distal end 172A and first point 184A, and between second distal end 172B and second point 184B, are straight when stent 120 is in its radially-compressed state (Stage 4), when stent 120 is in its radially-expanded state (Stage 1), and/or when stent 120 is in a partially-compressed state (such as Stages 2 and/or 3).

Alternatively, first and second primary segments 162A and 162B and/or these portions of first and second secondary segments 170A and 170B are curved in one or more of these states, such as described hereinbelow with reference to FIG. 8.

Figure 6:
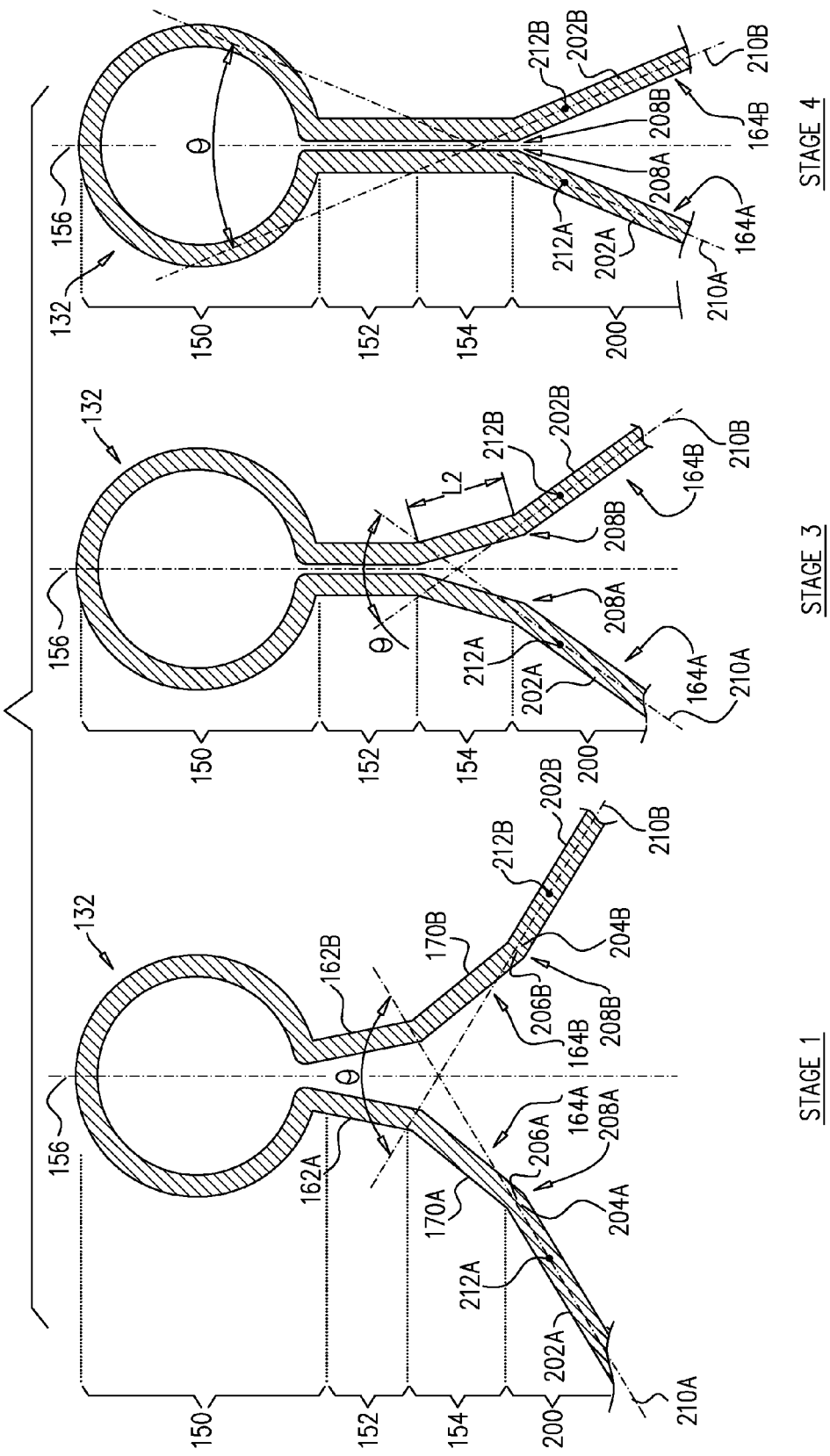
FIG. 6 is a schematic illustration of another configuration of a single strain-concentration module of the stent of the endovascular system of FIG. 4, in three radial-expansion states, in accordance with an application of the present invention.

Reference is now made to FIG. 6, which is a schematic illustration of another configuration of a single one of strain-concentration modules 132 of stent 120 of FIG. 4, in three radial-expansion states, in accordance with an application of the present invention. Except as described below, this configuration of strain-concentration module 132 is generally similar to the configuration described hereinabove with reference to FIGS. 5A-B. For clarity of illustration, Stage 2, although actually present in implementations of stent 120, has been omitted from FIG. 6; Stage 2 is similar to Stage 2 shown in FIGS. 5A-B, mutatis mutandis. In the configuration shown in FIG. 6, secondary section 154 is a secondary neck section, and strain-concentration module 132 further comprises a tertiary section 200. Tertiary section 200 comprises first and second tertiary segments 202A and 202B of first and second struts 164A and 164B, respectively, disposed on opposite sides of central axis 156. First and second distal ends 204A and 204B of first and second tertiary segments 202A and 202B, respectively, are connected to first and second proximal ends 206A and 206B of first and second secondary segments 170A and 170B at first and second tertiary junctions 208A and 208B, respectively. Typically, each of first and second secondary segments 170A and 170B has a length L2 (labeled in Stage 3) equal to at least 33%, such as at least 66%, of greatest outer width W of open loop section 150, no more than 300% of W, and/or between 33% and 300% of W. For some applications, tertiary section 200 is symmetrical about central axis 156 (as shown), while for other applications, the tertiary neck section is not symmetrical about the central axis (not shown).

First tertiary segment 202A defines a first tertiary straight line 210A, which passes through (i) first distal end 204A of first tertiary segment 202A and (ii) a third point 212A on first tertiary segment 202A at second distance D2 from first distal end 204A of first tertiary segment 202A, and second tertiary segment 202B defines a second tertiary straight line 210B, which passes through (i) second distal end 204B of second tertiary segment 202B and (ii) a fourth point 212B on second tertiary segment 202B at second distance D2 from second distal end 204B of second tertiary segment 202B. As mentioned above, second distance D2 equals 25% of greatest outer width W. (First and second tertiary lines 210A and 210B may thus be considered approximate representations of a longitudinal axis of first and second tertiary segments 202A and 202B, respectively, in respective vicinities of first and second distal ends 172A and 172B.) First tertiary line 210A defines a tertiary angle θ (theta) with second tertiary line 210B. (Points 184A and 184B are geometrical reference points, which are typically not actually marked on stent 120.)

As mentioned above, Stages 1, 2, 3, and 4 represent three consecutively increasing levels of compression of stent 120. Stent 120 is typically configured such that:

when the stent is in Stage 4, its radially-compressed state, typically: (a) primary angle α (alpha) has a compressed value of between 0 and 5 degrees, e.g., 0 degrees, (b) secondary angle β (beta) has a compressed value of between 0 and 5 degrees, or between 3 and 20 degrees, and/or greater than the compressed value of primary angle α (alpha) (angle α (alpha) and angle β (beta) are labeled in FIG. 5B, but not labeled in FIG. 6 for the sake of clarity), and (c) tertiary angle θ (theta) has a compressed value of at least 4 degrees, no more than 25 degrees, and/or between 4 and 25 degrees, and/or at least 5% greater than the compressed value of angle β (beta).

when the stent is in Stage 3, an state of partial radial compression, typically (a) primary angle α (alpha) has a partially-compressed value of between 0 and 10 degrees, e.g., 0 degrees, (b) secondary angle β (beta) has a partially-compressed value that is (i) greater than the partially-compressed value of primary angle α (alpha), such as at least 5 degrees, e.g., at least 10 degrees, greater than the partially-compressed value of primary angle α (alpha), and/or (ii) at least 5 degrees, less than 90 degrees, e.g., less than 60 degrees, such as less than 20 degrees, and/or between 5 and 90 degrees, e.g., between 5 and 20 degrees, and (c) tertiary angle θ (theta) has a partially-compressed value of at least 5 degrees, e.g., at least 10 degrees, greater than the partially-compressed value of secondary angle β (beta). It is noted that, as mentioned above, stent 120 assumes a plurality of partially radially-compressed states; the above-mentioned properties apply to at least one of these states, and generally to many of these states.

when the stent is in Stage 1, its radially-expanded state, and Stage 2, another state of partial radial compression, typically (a) primary angle α (alpha) typically has an expanded value that is (i) greater than the compressed value of primary angle α (alpha), such as at least 5 degrees greater than the compressed value of primary angle α (alpha), and/or (ii) at least 5 degrees, less than 90 degrees, such as less than 60 degrees, and/or between 5 and 90 degrees, e.g., between 5 and 60 degrees, (b) secondary angle β (beta) has an expanded value that is (i) greater than the expanded value of primary angle α (alpha), such as at least 5 degrees greater than the expanded value of primary angle α (alpha), and/or (ii) at least 10 degrees, less than 120 degrees, e.g., less than 90 degrees, and/or between 10 and 120 degrees, e.g., between 10 and 90 degrees, and (c) tertiary angle θ (theta) has an expanded value that is greater than the expanded value of secondary angle β (beta) (e.g., at least 5 degrees greater than the expanded value of secondary angle β (beta) and/or at least 105%, e.g., at least 120%, of the expanded value of secondary angle β (beta)), and/or is at least 7 degrees, less than 180 degrees, e.g., less than 135 degrees, and/or between 7 and 135 degrees.

As stent 120 is radially compressed (such as by crimping), the resulting strain on the stent is accumulated as described hereinabove with reference to FIGS. 5A-B. In addition, for some applications, the strain is accumulated in a fourth phase, subsequent to the third phase, in which the strain is primarily accumulated at first and second tertiary junctions 208A and 208B, i.e., at the interfaces between secondary neck section 154 and tertiary section 200.

Such distribution of stress helps prevent plastic (non-elastic) deformation of stent 120 when the stent is radially compressed, which could cause the stent to not return to its original shape upon subsequent radial expansion during implantation. This stress distribution may be particularly important in stents that are highly compressed (e.g., crimped) to provide a highly reduced crossing profile for percutaneous delivery. The configurations of stent 20 shown in FIGS. 1-3 generally do not provide such effective stress distribution, which may result in plastic deformation if stent 20 is highly radially compressed.

For some applications, as shown in FIG. 6, first and second secondary segments 170A and 170B of secondary neck section 154 are straight when stent 120 is in its radially-compressed state (Stage 4), when stent 120 is in its radially-expanded state (Stage 1), and/or when stent 120 is in a partially radially-expanded state (such as Stages 2 and/or 3). For some applications, as shown in FIG. 6, respective portions of first and second tertiary segments 202A and 202B of tertiary section 200, between first distal end 204A and third point 212A, and between second distal end 204B and fourth point 212B, are straight when stent 120 is in its radially-compressed state (Stage 4), when stent 120 is in its radially-expanded state (Stage 1), and/or when stent 120 is in a partially-compressed state (such as Stages 2 and/or 3). Alternatively, first and second secondary segments 170A and 170B and/or these portions of first and second tertiary segments 202A and 202B are curved in one or more of these states, such as described hereinbelow with reference to FIG. 8 regarding first and second primary segments 162A and 162B and/or portions of first and second secondary segments 170A and 170B, mutatis mutandis.

For some applications, first and second struts 164A and 164B together define additional neck sections proximally beyond secondary neck section 154. These additional neck sections are typically arranged with respect to their more distal neck segment and more proximal strut segments as described hereinabove regarding the relationship of secondary neck section 154 with more distal primary neck section 152 and more proximal tertiary section 200, mutatis mutandis.

Figure 7:
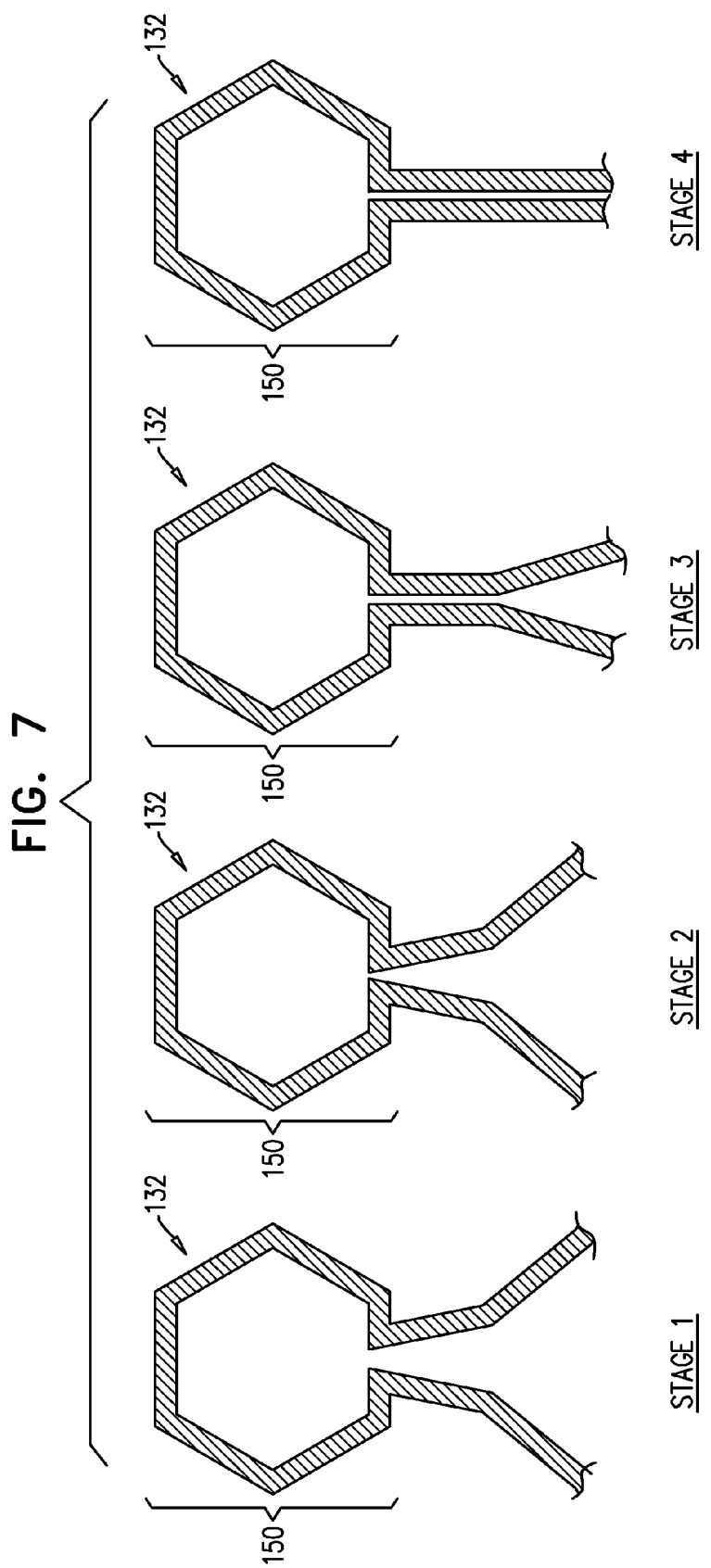
FIG. 7 is a schematic illustration of yet another configuration of a single strain-concentration module of the stent of the endovascular system of FIG. 4, in four radial-expansion states, in accordance with an application of the present invention.

Reference is made to FIG. 7, which is a schematic illustration of yet another configuration of a single strain-concentration module 132 of stent 120 of FIG. 4, in four radial-expansion states, in accordance with an application of the present invention. This configuration is generally similar to the configuration described hereinabove with reference to FIGS. 5A-B or FIG. 6, except that open loop section 150 is shaped as a hexagon. In contrast, in the configurations shown in FIGS. 5A-B and 6, open loop section 150 is generally circular. Alternatively, open loop section 150 may have another shape, such as an ellipse, a polygon, or an irregular shape. For some applications, open loop section 150 is symmetrical about central axis 156 (as shown), while for other applications, the open loop section is not symmetrical about the central axis (not shown).

Figure 8:
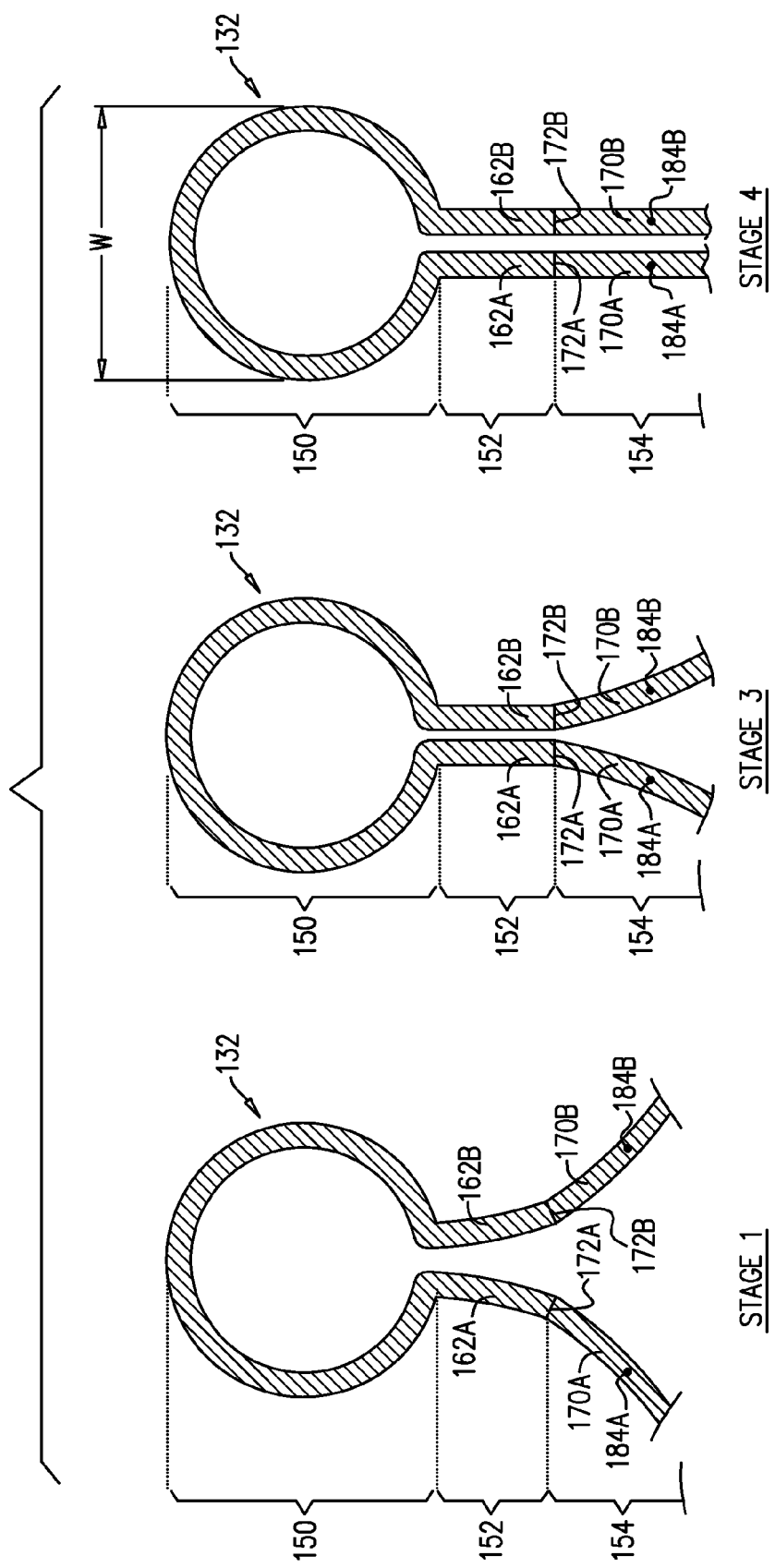
FIG. 8 is a schematic illustration of a single strain concentration module of a stent of the endovascular system of FIG. 4, in three radial-expansion states, in accordance with an application of the present invention.

Reference is now made to FIG. 8, which is a schematic illustration of a single one of strain concentration modules 132 of stent 120 of FIG. 4, in three radial-expansion states, in accordance with an application of the present invention. In this configuration, strain concentration module 132 is generally similar to the configuration described hereinabove with reference to FIGS. 5A-B, except as follows. For clarity of illustration, Stage 2, although actually present in implementations of stent 120, has been omitted from FIG. 8; Stage 2 is similar to Stage 2 shown in FIGS. 5A-B, mutatis mutandis. In this configuration, first and second primary segments 162A and 162B of primary neck section 152 are curved when stent 120 is in its radially-expanded state (Stage 1), and straight when the stent is in a partially-compressed state (such as Stages 2 and/or 3) and its radially-compressed state (Stage 4). Alternatively or additionally, respective portions of first and second secondary segments 170A and 170B of secondary section 154, between first distal end 172A and first point 184A, and between second distal end 172B and second point 184B, are curved when stent 120 is in its radially-expanded state (Stage 1) and/or when stent 120 is in a partially-compressed state (such as Stages 2 and/or 3), and straight when stent 120 is in its radially-compressed state (Stage 4).

As described hereinabove with reference to FIGS. 5A-B, for some applications, radii of curvature of first and second struts 164A and 164B at first and second secondary junctions 176A and 176B, respectively, are less than 50% (e.g., less than 25%) of a length of first primary segment 162A and 50% (e.g., less than 25%) of a length of second primary segment 162B, respectively, when the stent is in its radially-expanded state.

Reference is now made to FIG. 9, which is a schematic planar projection of a stent pattern 300, in accordance with an application of the present invention. Stent pattern 300 comprises a plurality of circumferential bands 122, each of which comprises a plurality of struts 24. Bands 122 are interconnected by interconnecting struts 25. Each of circumferential bands 122 comprises a plurality of strain-concentration modules 132. In the configuration shown in FIG. 9, the strain-concentration modules of each band are alternatingly directed in opposite longitudinal directions (distally, proximally, distally, proximally, etc.). Strain-concentration modules 132 may be configured as described hereinabove with reference to FIGS. 5A-B (as shown in FIG. 9), FIG. 6 (not shown in FIG. 9), FIG. 7 (not shown in FIG. 9), and/or FIG. 8 (not shown in FIG. 9). Stent pattern 300 is shown in a non-radially-compressed state, as described in more detail below.

For some applications, first and second proximal ends 206A and 206B of first and second secondary segments 170A and 170B (labeled in FIG. 6), respectively, are directly or indirectly connected to another one of circumferential bands 122. For some applications, none of struts 24, other than first and second struts 164A and 164B, is connected to first primary junction 168A or second primary junction 168B, of a given strain-concentration module 132. Alternatively or additionally, for some applications, none of struts 24, other than first and second struts 164A and 164B, is connected to first secondary junction 176A or second secondary junction 176B.

For some applications, during manufacture, stent 120 is cut from a superelastic (typically Nitinol) tube having a size (e.g., diameter) less than the size of stent 120 in its fully radially-expanded state upon the completion of manufacture. The stent is subsequently heat-set to a desired, larger radially-expanded size on a heat-setting jig. This radially-expanded state becomes the radially-relaxed state of the stent. The stent is then crimped into a fully radially-reduced size, which is smaller (e.g., has a smaller diameter) than the initial as-cut size prior to heat-setting. The initial size of the tube is typically between the fully-expanded size after heat-setting and the crimped radially-reduced size. This intermediary size reduces the required amount of superelastic alloy (which is generally expensive), and also introduces less mechanical strain into the stent than would have been introduced if the initial tube had been of the same size as the final radially-reduced size. For example, for applications in which stent 120 is used as an aortic stent, the stent may be cut from a tube having an internal diameter of 12 mm, heat-set to an internal diameter of approximately 28 mm, and then crimped to an internal diameter of approximately 4 mm. Stent pattern 300, shown in FIG. 9, is an exemplary pattern for the stent as-cut, before heat-setting and crimping.

For some applications, endovascular systems 10 and/or 110 are used to treat an aneurysm, such as an aortic aneurysm, or an aneurism of another blood vessel. For example, the aneurism may be of the sub-renal aorta. For some applications, a method is provided that comprises identifying that a patient suffers from an aneurysm, such as an aortic aneurysm (e.g., a sub-renal aortic aneurism), and, responsively to the identifying, endoluminally introducing endovascular systems 10 and/or 110 responsively to the identifying. Techniques for identifying that a patient suffers from an aneurism are well known, and thus not described herein.

For some applications, endovascular systems 10 and/or 110 are deployed in the common iliac arteries in a vicinity of a bifurcation with the descending abdominal aorta, or in other body lumens, such as at other branching body lumens. For example, endovascular systems and/or 110 may be deployed in the aortic arch in a vicinity of one of the branches of the aortic arch, and also as a fenestrated endovascular system between the common carotid artery and either the internal or external carotid artery, and/or as an additional endovascular system between the fenestration of the aforementioned stent and the other carotid artery.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

PCT Application PCT/IL2008/000287, filed Mar. 5, 2008, which published as PCT Publication WO 2008/107885 to Shalev et al., and U.S. application Ser. No. 12/529,936 in the national stage thereof, which published as US Patent Application Publication 2010/0063575 to Shalev et al.

U.S. Provisional Application 60/892,885, filed Mar. 5, 2007

U.S. Provisional Application 60/991,726, filed Dec. 2, 2007

U.S. Provisional Application 61/219,758, filed Jun. 23, 2009

U.S. Provisional Application 61/221,074, filed Jun. 28, 2009

PCT Application PCT/IB2010/052861, filed Jun. 23, 2010, which published as PCT Publication WO 2010/150208

PCT Application PCT/IL2010/000564, filed Jul. 14, 2010, which published as PCT Publication WO 2011/007354

PCT Application PCT/IL2010/000917, filed Nov 4, 2010, which published as PCT Publication WO 2011/055364

PCT Application PCT/IL2010/000999, filed Nov. 30, 2010, which published as PCT Publication WO 2011/064782

PCT Application PCT/IL2010/001018, filed Dec. 2, 2010, which published as PCT Publication WO 2011/067764

PCT Application PCT/IL2010/001037, filed Dec. 8, 2010, which published as PCT Publication WO 2011/070576

PCT Application PCT/IL2011/000135, filed Feb. 8, 2011, which published as PCT Publication WO 2011/095979

U.S. application Ser. No. 13/031,871, filed Feb. 22, 2011, which published as US Patent Application Publication 2011/0208289

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising a stent (120) having proximal and distal ends (140, 142), which is configured to assume radially-compressed and radially-expanded states, and which comprises a plurality of circumferential bands (122) disposed about a longitudinal axis (123) of the stent (120), each of which bands (122) comprises a plurality of struts (124) connected to one another, wherein at least one of the bands (122) is shaped so as to define a plurality of distally-directed peaks (126) alternating with a plurality of proximally-directed troughs (128), and one or more strain-concentration modules (132), each of which modules (132) has a central axis (156) parallel to the longitudinal axis (123) of the stent (120), and comprises:

an open loop section (150), which (a) comprises one of the distally-directed peaks (126), and (b) is shaped so as to define first and second proximal open loop ends (160A, 160B) disposed on opposite sides of the central axis (156), wherein, when the stent (120) is in its radially-compressed state, the open loop section (150) has a greatest outer width (W) measured perpendicular to the central axis (156), and a first distance (D1) between the first and the second proximal open loop ends (160A, 160B) is less than 20% of the greatest outer width (W);

a primary neck section (152), which comprises first and second primary segments (162A, 162B) of first and second ones of the struts (164A, 164B), respectively, disposed on opposite sides of the central axis (156), wherein first and second distal ends (166A, 166B) of the first and the second primary segments (162A, 162B) are connected to the first and the second proximal open loop ends (160A, 160B) at first and second primary junctions (168A, 168B), respectively, and wherein each of the first and the second primary segments (162A, 162B) has a length (L1) equal to at least 33% of the greatest outer width (W) of the open loop section (150); and a secondary section (154), which comprises first and second secondary segments (170A, 170B) of the first and the second struts (164A, 164B), respectively, disposed on opposite sides of the central axis (156), wherein first and second distal ends (172A, 172B) of the first and the second secondary segments (170A, 170B), respectively, are connected to first and second proximal ends (174A, 174B) of the first and the second primary segments (170A, 170B) at first and second secondary junctions (176A, 176B), respectively, wherein the first primary segment (162A) defines a first primary straight line (180A), which passes through the first distal end (166A) and the first proximal end (174A) of the first primary segment (162A), and the second primary segment (162B) defines a second primary straight line (180B), which passes through the second distal end (166B) and the second proximal end (174B) of the second primary segment (162B), wherein the first primary line (180A) defines a distal-facing primary angle (α) with the second primary line (180B) which (i) has a compressed value of between 0 and 5 degrees, when the stent (120) is in its radially-compressed state, and (ii) has an expanded value that is between (x) 5 degrees greater than the compressed value of the primary angle (α) and (y) 60 degrees, when the stent (120) is in its radially-expanded state, wherein the first secondary segment (170A) defines a first secondary straight line (182A), which passes through (i) the first distal end (172A) of the first secondary segment (170A) and (ii) a first point (184A) on the first secondary segment (170A) at a second distance (D2) from the first distal end (172A) of the first secondary segment (170A), and the second secondary segment (170B) defines a second secondary straight line (182B), which passes through (i) the second distal end (172B) of the second secondary segment (170B) and (ii) a second point (184B) on the second secondary segment (170B) at the second distance (D2) from the second distal end (172B) of the second secondary segment (170B), which second distance (D2) equals 25% of the greatest outer width (W), and wherein the first secondary line (182A) defines a distal-facing secondary angle (β) with the second secondary line (182B) which (i) has a compressed value of between 0 and 5 degrees, when the stent (120) is in its radially-compressed state, and (ii) has an expanded value that is greater than the expanded value of the primary angle (α), when the stent (120) is in its radially-expanded state.

2. The apparatus according to claim 1, wherein the expanded value of the secondary angle (β) is between (x) 5 degrees greater than the expanded value of the primary angle (α) and (y) 90 degrees.

3. The apparatus according to claim 1, wherein radii of curvature of the first and the second struts (164A, 164B) at the first and the second secondary junctions (176A, 176B), respectively, are less than 50% of a length of the first primary segment (162A) and 50% of a length of the second primary segment (162B), respectively, when the stent (120) is in its radially-expanded state.

4. The apparatus according to claim 1, wherein the stent (120) is configured to assume a plurality of partially radially-compressed states between its radially-compressed and its radially-expanded states, and wherein, when the stent (120) is in at least one of its partially radially-compressed states, the primary angle (α) has a partially-compressed value of between 0 and 10 degrees, and the secondary angle (β) has a partially-compressed value that is greater than the partially-compressed value of the primary angle (α).

5. The apparatus according to claim 1, wherein none of the struts (124), other than the first and the second struts (164A, 164B), is connected to the first primary junction (168A) or the second primary junction (168B).

6. The apparatus according to claim 1, wherein none of the struts (124), other than the first and the second struts (164A, 164B), is connected to the first secondary junction (176A) or the second secondary junction (176B).

7. The apparatus according to claim 1, wherein the first and the second primary segments (162A, 162B) of the primary neck section (152) are straight when the stent (120) is in its radially-compressed state.

8. The apparatus according to claim 1, wherein the first and the second primary segments (162A, 162B) of the primary neck section (152) are straight when the stent (120) is in its radially-expanded state.

9. The apparatus according to claim 1, wherein the first and the second primary segments (162A, 162B) of the primary neck section (152) are curved when the stent (120) is in its radially-expanded state, and are straight when the stent (120) is in its radially-compressed state.

10. The apparatus according to claim 1, wherein the stent (120) is shaped so as to generally define a cylinder when in its radially-expanded state, and wherein the struts (124) of the strain-concentration modules (132) coincide with a surface of the cylinder.

11. The apparatus according to claim 1, wherein the at least one of the bands (122) is serpentine at least when the stent (120) is in its radially-expanded state.

12. The apparatus according to claim 1, wherein the at least one of the bands (122) extends around an entire circumference of the stent (120).

13. The apparatus according to claim 1, wherein a length of the open loop section, measured along a perimeter thereof, is at least 0.7 mm.

14. The apparatus according to claim 1, wherein first and second proximal ends (174A, 174B) of the first and second secondary segments (170A, 170B), respectively, are directly or indirectly connected to another one of the bands (122).

15. The apparatus according to claim 1,
wherein the secondary section (154) is a secondary neck section (154),
wherein each of the first and second secondary segments (170A, 170B) has a length equal to at least 66% of the greatest outer width (W) of the open loop section (150),
wherein each of the one or more strain concentration modules (132) further comprises a tertiary section (200), which comprises first and second tertiary segments (202A, 202B) of the first and the second struts (164A, 164B), respectively, disposed on opposite sides of the central axis (156), wherein first and second distal ends (204A, 204B) of the first and the second tertiary segments (202A, 202B), respectively, are connected to first and second proximal ends (206A, 206B) of the first and the second secondary segments (170A, 170B) at first and second tertiary junctions (208A, 208B), respectively, wherein the first tertiary segment (202A) defines a first tertiary straight line (210A), which passes through (i) the first distal end (204A) of the first tertiary segment (202A) and (ii) a third point (212A) on the first tertiary segment (202A) at the second distance (D2) from the first distal end (204A) of the first tertiary segment (202A), and the second tertiary segment (202B) defines a second tertiary straight line (210B), which passes through (i) the second distal end (204B) of the second tertiary segment (202B) and (ii) a fourth point (212B) on the second tertiary segment (202B) at the second distance (D2) from the second distal end (204B) of the second tertiary segment (202B), and wherein the first tertiary line (210A) defines a tertiary angle ($\theta$) with the second tertiary line (210B) which (i) has a compressed value of at least 105% of the compressed value of angle $\beta$ (beta), when the stent is in its radially-compressed state, and (ii) has an expanded value that is between (x) 120% of the expanded value of the secondary angle ($\beta$) and (y) 135 degrees, when the stent (120) is in its radially-expanded state.

16. The apparatus according to claim 15, wherein the first and the second secondary segments (170A, 170B) of the secondary neck section (154) are straight when the stent (120) is in its radially-compressed state.

17. The apparatus according to claim 15, wherein the first and the second secondary segments (170A, 170B) of the secondary neck section (154) are straight when the stent (120) is in its radially-expanded state.

18. The apparatus according to claim 1, wherein the stent (120) comprises a metal.

19. The apparatus according to claim 18, wherein the metal comprises a superelastic alloy.

20. The apparatus according to claim 19, wherein the superelastic alloy comprises Nitinol.

21. The apparatus according to claim 1, wherein the stent (120) is self-expanding from the radially-compressed state to the radially-expanded state.

22. The apparatus according to claim 1, wherein the radially-expanded relaxed state of the stent (120) is achieved by heat-setting of the stent (120) in the radially-expanded state that is more radially expanded than an initial as-cut state of the stent (120).

23. The apparatus according to claim 1, wherein the circumferential bands (122) comprise a plurality of substantially M-shaped segments.

24. The apparatus according to claim 1, wherein the circumferential bands (122) are adjacently connected therebetween.

25. The apparatus according to claim 1, further comprising a graft member (30), which covers at least a portion of the stent (120) and is securely connected thereto.

* * * * *